(12) United States Patent
Inoue

(10) Patent No.: US 6,514,282 B1
(45) Date of Patent: Feb. 4, 2003

(54) METHOD OF FOLDING TRANSPLANTING INSTRUMENT AND TRANSPLANTING INSTRUMENT

(76) Inventor: Kanji Inoue, 98-13, Miyazaki-cho Shimogamo, Sakyo-ku, Kyoto-shi, Kyoto 606-0802 (JP)

(*) Notice: Subject to any disclaimer, the term of this patent is extended or adjusted under 35 U.S.C. 154(b) by 0 days.

(21) Appl. No.: 09/857,441

(22) PCT Filed: Oct. 4, 1999

(86) PCT No.: PCT/JP99/05484

§ 371 (c)(1),
(2), (4) Date: Jun. 4, 2001

(87) PCT Pub. No.: WO01/24732

PCT Pub. Date: Apr. 12, 2001

(51) Int. Cl.[7] .................................................. A61F 2/06
(52) U.S. Cl. ..................................... 623/1.13; 623/1.44
(58) Field of Search ................................ 623/1.1, 1.11, 623/1.13, 1.15, 116, 1.18, 1.23

(56) References Cited

U.S. PATENT DOCUMENTS

| | | |
|---|---|---|
| 3,304,557 A | 2/1967 | Polansky |
| 4,300,244 A | 11/1981 | Bokros |
| 4,313,231 A | 2/1982 | Koyamada |
| 4,338,934 A | 7/1982 | Spademan |
| 4,872,874 A | 10/1989 | Taheri |
| 5,098,406 A | 3/1992 | Sawyer |
| 5,104,399 A | 4/1992 | Lazarus |
| 5,151,105 A | 9/1992 | Kwan-Gett |
| 5,183,085 A | 2/1993 | Timmermans |
| 5,199,948 A | 4/1993 | McPhee |
| 5,207,695 A | 5/1993 | Trout, III |
| 5,234,456 A | 8/1993 | Silvestrini |
| 5,236,447 A | 8/1993 | Kubo et al. |
| 5,242,452 A | 9/1993 | Inoue |
| 5,290,305 A | 3/1994 | Inoue |

(List continued on next page.)

FOREIGN PATENT DOCUMENTS

| | | |
|---|---|---|
| DE | 4219949 | 12/1993 |
| EP | 0472731 | 3/1992 |
| EP | 0786267 A1 | 7/1997 |
| EP | 0858784 A2 | 8/1998 |
| EP | 0933070 A2 | 8/1999 |
| GB | 2164562 | 3/1986 |
| JP | 3-236836 | 10/1991 |
| JP | 0 464 755 A1 | 1/1992 |
| JP | 4-25755 | 2/1992 |
| JP | 4-263852 | 9/1992 |
| JP | 5-212121 | 8/1993 |
| JP | 7-24072 | 1/1995 |
| JP | 3009638 | 2/1995 |

OTHER PUBLICATIONS

Kanji Inoue, et al., Aortic Arch Reconstruction by Transluminally Placed Endovascular Branched Stent Graft, Nov. 9, 1999, pp. II–316–321, vol. 100, No. 19, *Circulation* Supplement, Lippincott Williams & Wilkins.

*Primary Examiner*—David J. Isabella
*Assistant Examiner*—Hieu Phan
(74) *Attorney, Agent, or Firm*—Banner & Witcoff, Ltd.

(57) ABSTRACT

An implantable appliance (1) comprises a front end wire ring (2), one or more intermediate wire rings (5) and a rear end wire ring (3) connected by a tubular cover (4). The wire rings (2), (3) and (5) are flexibly foldable. A front end portion (1a) of the appliance (1) is equally divided into four or an even number over four segments with dividing points (6a), (6b), (6c), (6d) between the segments, and a front hooking portion (8) for hauling the appliance (1) is formed at midpoints between the dividing points (6a), (6b), (6c), (6d) and the dividing points (6b), (6c), (6d), (6a). The invention includes a method in which the front end portion (1a) is collapsed into a wavy shape with every other dividing point (6a), (6c) forming forwardly directed peaks and other dividing points (6b), (6d) forming the bottoms of forwardly directed valleys, such that front hooking portions are located between adjacent peaks and valleys.

22 Claims, 22 Drawing Sheets

U.S. PATENT DOCUMENTS

| | | |
|---|---|---|
| 5,330,528 A | 7/1994 | Lazim |
| 5,383,926 A | 1/1995 | Lock et al. |
| 5,387,235 A | 2/1995 | Chuter |
| 5,405,331 A | 4/1995 | Behnke et al. |
| 5,507,767 A | 4/1996 | Maeda et al. |
| 5,507,771 A | 4/1996 | Gianturco |
| 5,520,641 A | 5/1996 | Behnke et al. |
| 5,538,505 A | 7/1996 | Weinstein et al. |
| 5,554,181 A | 9/1996 | Das |
| 5,562,724 A | 10/1996 | Vowerk et al. |
| 5,569,205 A | 10/1996 | Hart et al. |
| 5,607,445 A | 3/1997 | Summers |
| 5,609,628 A | 3/1997 | Keranen |
| 5,628,783 A | 5/1997 | Quiachon et al. |
| 5,665,117 A | 9/1997 | Rhodes |
| 5,676,671 A | 10/1997 | Inoue |
| 5,693,089 A | 12/1997 | Inoue |
| 5,755,772 A | 5/1998 | Evans et al. |
| 5,755,773 A | 5/1998 | Evans et al. |
| 5,782,904 A | 7/1998 | White et al. |
| 5,824,037 A | 10/1998 | Fogarty et al. |
| 5,843,162 A | 12/1998 | Inoue |
| 5,925,076 A * | 7/1999 | Inoue ................. 606/108 |
| 5,951,585 A * | 9/1999 | Cathcart et al. ............ 606/198 |
| 5,976,179 A | 11/1999 | Inoue |
| 6,013,100 A | 1/2000 | Inoue |
| 6,183,503 B1 * | 2/2001 | Hart et al. ................... 606/198 |
| 6,183,504 B1 | 2/2001 | Inoue |
| 6,245,097 B1 | 6/2001 | Inoue |
| 6,254,629 B1 | 7/2001 | Inoue |
| 6,254,630 B1 | 7/2001 | Inoue |
| 6,261,317 B1 | 7/2001 | Inoue |
| 6,270,520 B1 | 8/2001 | Inoue |
| 6,290,666 B1 * | 9/2001 | Devonec ..................... 604/540 |

FOREIGN PATENT DOCUMENTS

| | | |
|---|---|---|
| JP | 6-63155 | 3/1995 |
| JP | 9-506524 | 6/1995 |
| JP | 9-511160 | 11/1997 |
| JP | 10-506292 | 6/1998 |
| WO | 91/12047 | 8/1991 |
| WO | 95/05788 | 2/1995 |
| WO | WO 95/16406 | 6/1995 |
| WO | WO 95/21592 | 8/1995 |
| WO | WO 95/34255 | 12/1995 |
| WO | WO 96/36297 A1 | 11/1996 |
| WO | WO 96/36387 A1 | 11/1996 |

* cited by examiner

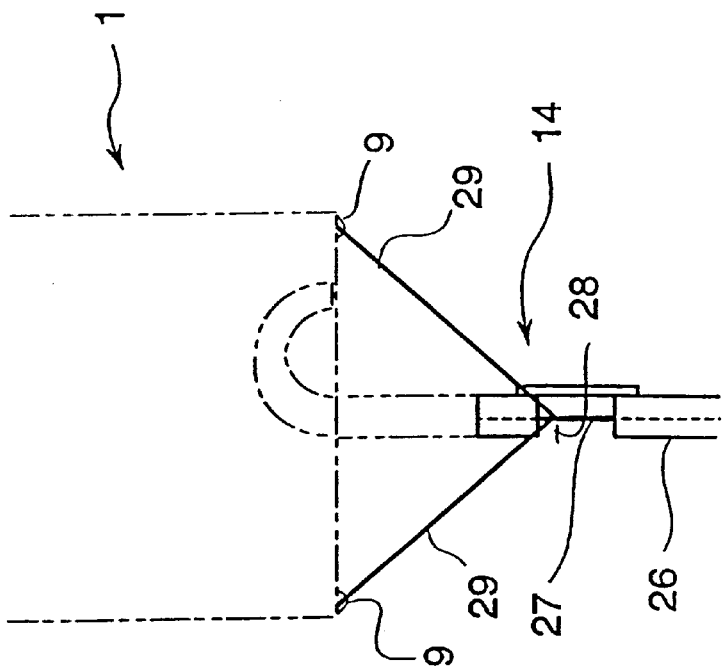
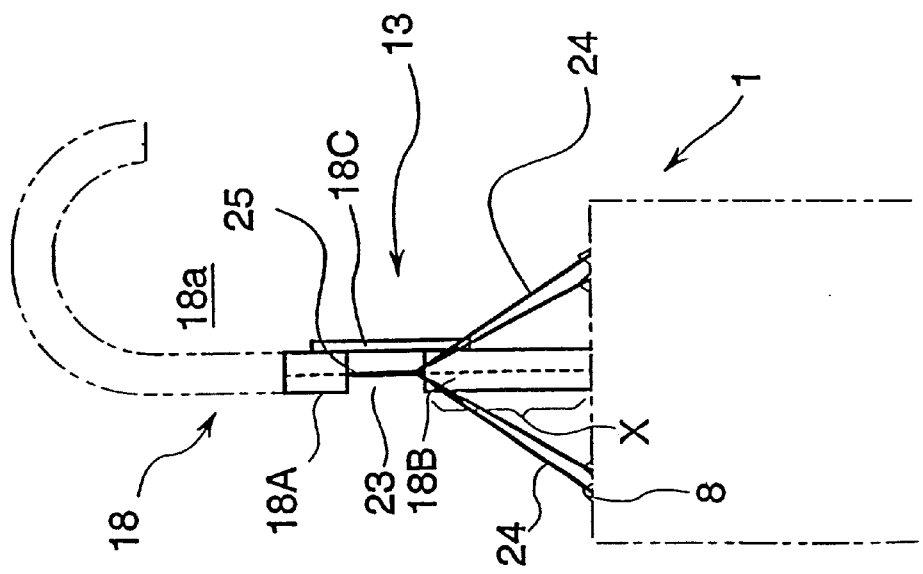

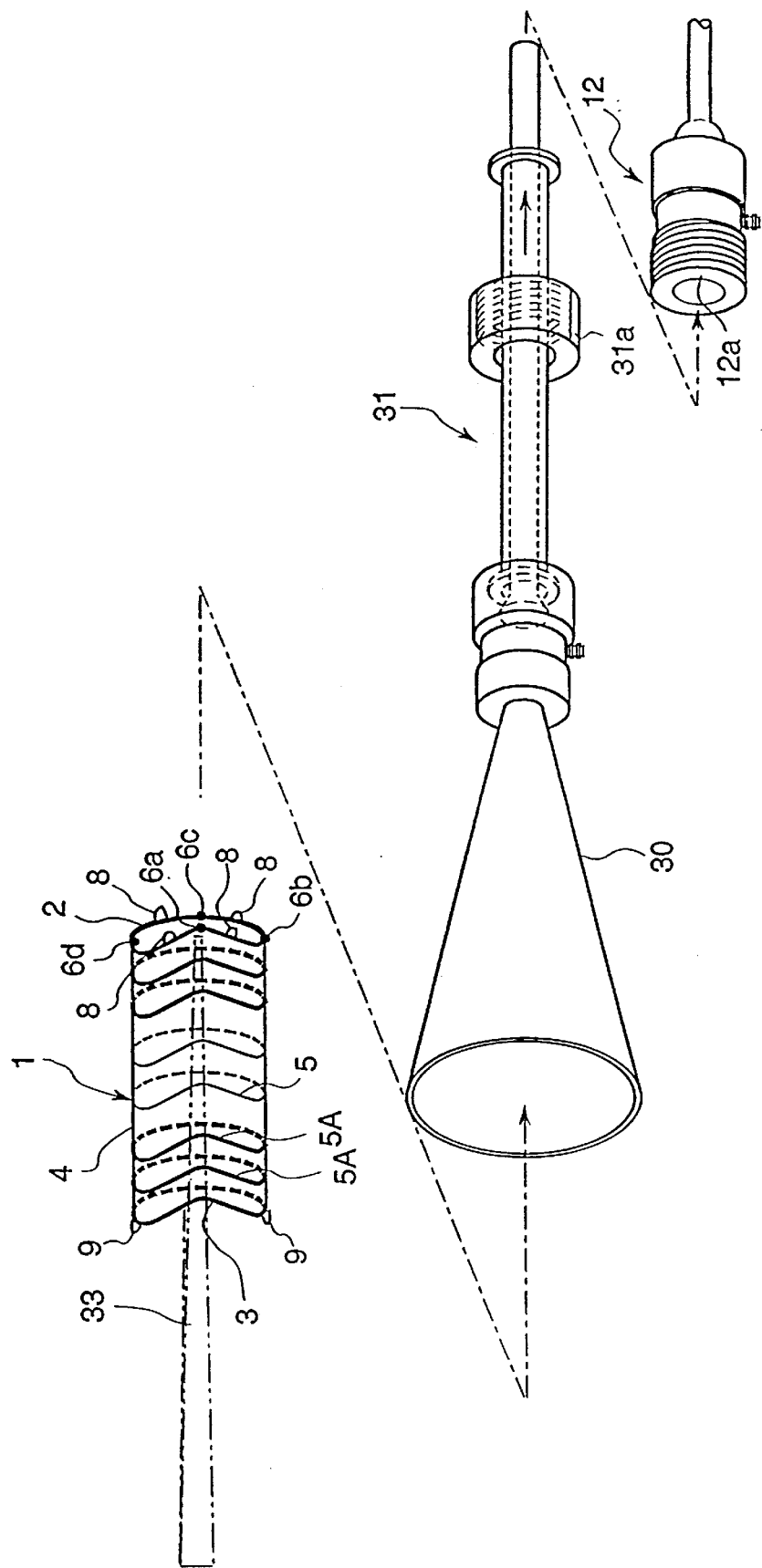

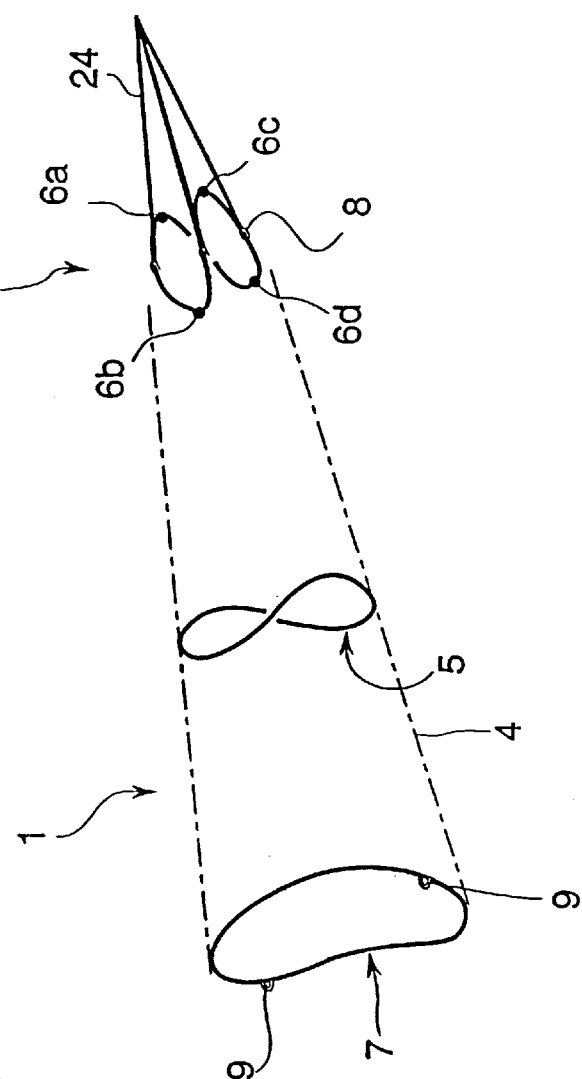
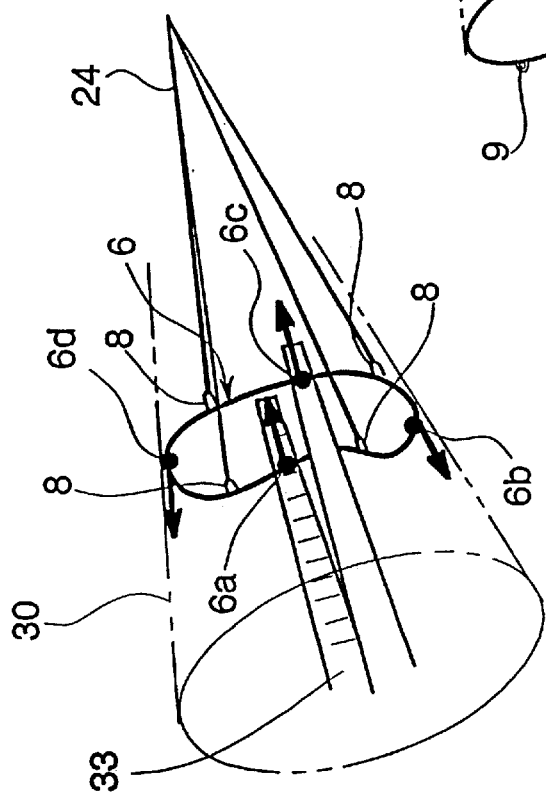

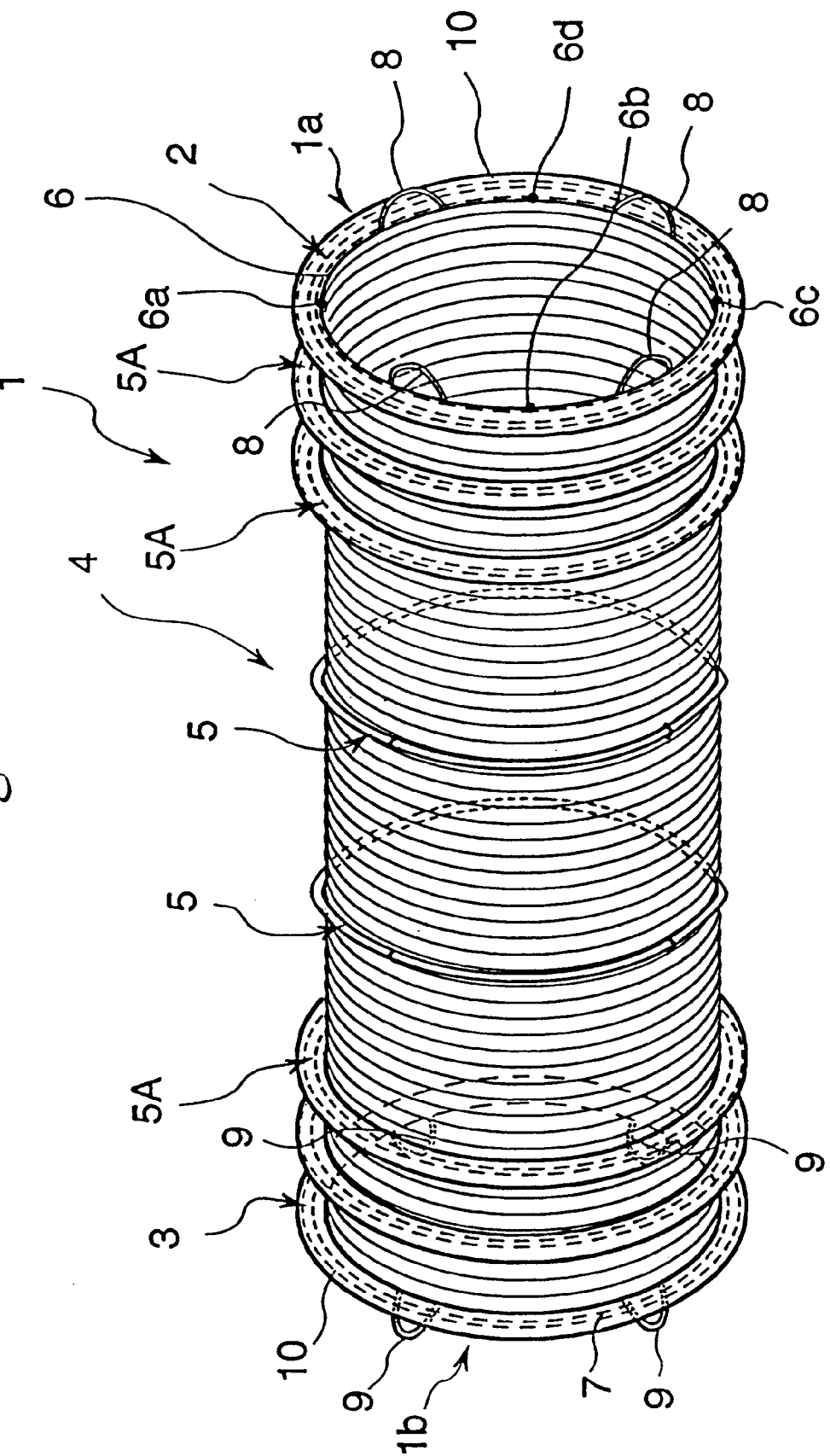

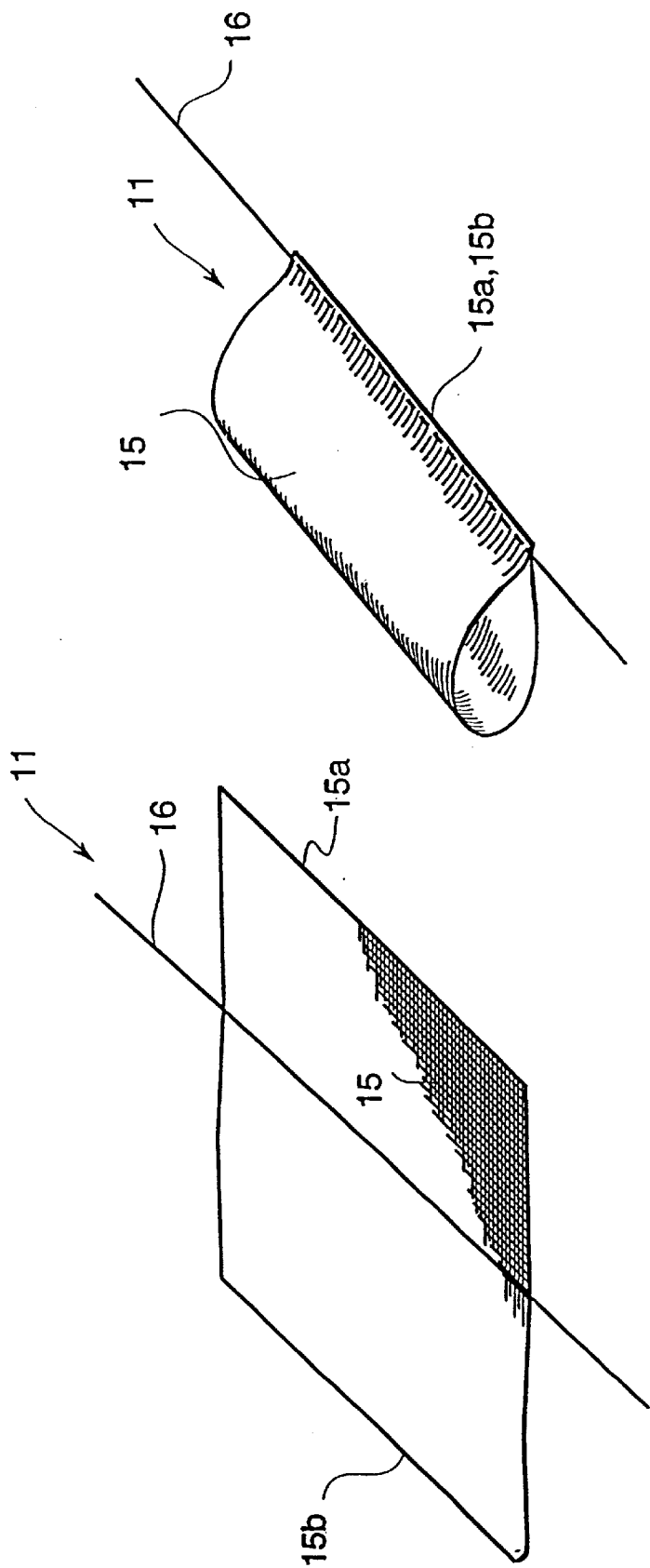

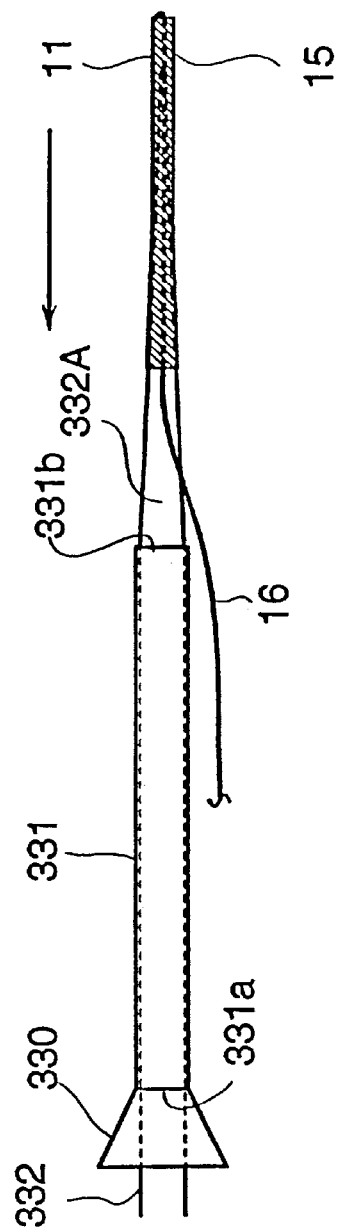
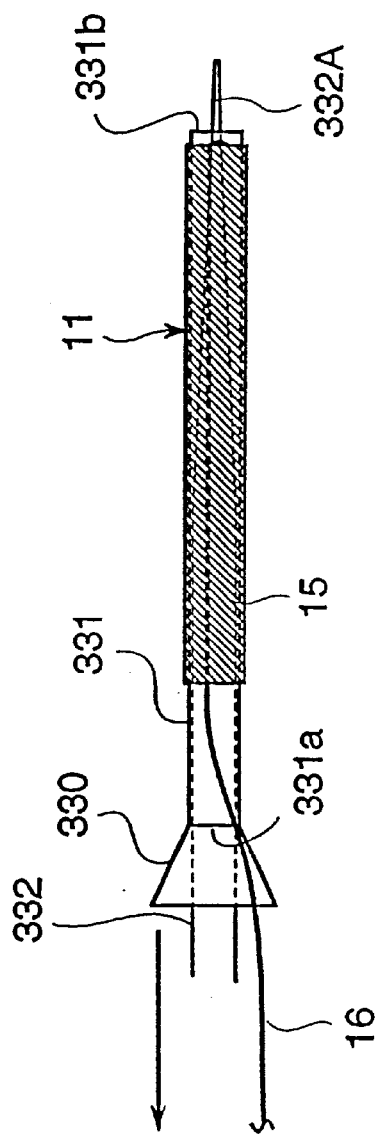
Fig.18
Fig.19

METHOD OF FOLDING TRANSPLANTING INSTRUMENT AND TRANSPLANTING INSTRUMENT

FIELD OF THE ART

This invention relates to a method of collapsing an appliance to be implanted which belongs to a field of medical devices (wherein the appliance collapsible for insertion into a human organ and capable of resilient restoration will be referred to as "an appliance to be implanted" in this specification and claims) and the appliance to be implanted.

BACKGROUND ART

With a recent progress of medical techniques, a technique enabling transvascular use of a variety of appliances such as artificial blood vessels without ventrotomy has reached a clinical stage. Specific examples of such a technique include a method of transferring and fixing an artificial blood vessel using a catheter which has been invented by the inventor of present claimed invention and disclosed in the paper (for example, PCT/JP96/01347 which has been published with International Publication No. WO96/36387). This method includes; inserting a catheter into a human body through an inguinal artery to position a front end thereof near an affected portion in which an aneurysm or the like is present, inserting a tubular artificial blood vessel provided with collapsible/restorable elasticity into the catheter in a collapsed condition, transporting the artificial blood vessel to a predetermined location near the affected portion by the use of a transporting device or a hauling device, and releasing the artificial blood vessel from the catheter at the location, thereby to position the artificial blood vessel in an affected blood vessel having the aneurysm.

In the above-described document, the appliance to be implanted comprises a front end wire ring, a rear end wire ring arranged facing to the front end wire ring, a tubular cover which connects the front end wire ring and the rear end wire ring, and a plurality of intermediate wire rings spaced apart from each other between the front end wire ring and the rear end wire ring in which the circumference of the front end wire ring is equally divided into four or an even number over four segments with dividing points between the segments and hooking portions are formed for a front pull string to be passed through at every other dividing point between the segments, the front end wire ring is folded into a wavy shape with the dividing points where the hooking portion is provided forming a forwardly directed peak and the other dividing points forming a bottom of a forwardly directed valley and the intermediate wire rings and the rear end wire ring are folded into a wavy shape having the same phase as that of the front end wire ring.

With the method of collapsing the artificial blood vessel, a number of the hooking portions for a front pull string equals to a number of peaks when collapsed. In the artificial blood vessel of the above arrangement if a number of the hooking portions is set to be small, for example, two, pulling force is difficult to be transferred uniformly to the artificial blood vessel when the artificial blood vessel is released from the catheter, which makes the artificial blood vessel tilt easily. As a result, it becomes difficult to release the artificial blood vessel with the front end wire ring opening at right angles to an axis of the artificial blood vessel. In addition, the artificial blood vessel might not be able to be restored into an appropriate original shape after released from the catheter due to a possible habit of the wire rings because a pulling force is concentrated on the peaks of the wire rings while the artificial blood vessel is transported in the catheter.

In order to solve the above problems, it can be conceived that the number of hooking portions is increased. However, in this arrangement the number of the peaks also increases inevitably, resulting in being bulky when collapsed. As a result, it is difficult to transport thus arranged artificial blood vessel stably without causing bulky when collapsed. In addition, it is impossible to get rid of stress concentration fully because the artificial blood vessel is hauled at a portion of the peak.

DISCLOURE OF THE INVENTION

In order to solve the above problems, in collapsing an appliance to be implanted comprising a front end wire ring, a rear end wire ring arranged facing to the front end wire ring, a tubular cover which connects the front end wire ring and the rear end wire ring, and an intermediate wire ring arranged between the front end wire ring and the rear end wire ring, in which each of the wire rings is given flexibly foldable elasticity, the present claimed invention is characterized by that circumference of a front end portion of the appliance to be implanted is equally divided into four or an even number over four segments with dividing points between the segments, a front hooking portion for hauling the appliance to be implanted is formed at midpoints between each adjacent two of the dividing points, the front end portion is collapsed into a wavy shape with every other dividing point forming a forwardly directed peak and other dividing point forming a bottom of a forwardly directed valley and the intermediate wire ring and the rear end wire ring are collapsed into a wavy shape having generally the same phase as that of the front end portion.

In order not to prevent the appliance to be implanted from being collapsed by the intermediate wire ring it is preferable that the appliance to be implanted is collapsed in a condition that the intermediate wire ring is fixed to the tubular cover at positions which generally correspond to the positions where the front hooking portions are provided.

In order to keep the collapsed condition for sure it is preferable that the appliance to be implanted is kept in a collapsed condition by a retaining means and the collapsed appliance to be implanted is restored into an original shape by releasing the retaining means at a target position.

In order to make it possible to release the appliance to be implanted from the collapsed condition in a remote place without fail it is preferable that the retaining means comprises a string which is wound around the collapsed appliance to be implanted and which has a loop at one portion thereof and a retaining rod which passes through the loop of the string, the appliance to be implanted is kept in the collapsed condition by passing the retaining rod through the loop of the string and the collapsed condition by means of the string is released by drawing the retaining rod out of the loop.

In case a rear hooking portion for hauling the appliance to be implanted is provided at a position which has generally the same phase as that of a position where a front hooking portion is provided on a rear end portion of the appliance to be implanted, it is preferable that the appliance to be implanted is collapsed so that the rear hooking portion locates at midpoints between the forwardly directed peaks and the bottoms of forwardly directed valleys when the rear end portion is collapsed to have generally the same phase as that of the front end portion.

In case a rear hooking portion for hauling the appliance to be implanted is provided at every other position which has generally the same phase as that of the dividing points on a rear end portion of the appliance to be implanted, it is preferable that the appliance to be implanted is collapsed so that the rear hooking portion locates at the bottoms of the forwardly directed valleys of the rear end portion when the rear end portion is collapsed to have generally the same phase as that of the front end portion.

In order to collapse the appliance to be implanted into a small size with ease it is effective if the front and rear end wire rings are connected with the tubular cover through a film member so that an annular gap at least formed between each of the front and rear end wire rings and the tubular cover is liquid-tightly sealed and the appliance to be implanted is collapsed with each of the front and rear end wire rings making a back and forth movement relative to the tubular cover within a certain range.

In order to secure an appropriate function of transportation and travel as well as to keep a collapsed condition in compact as much as possible it is preferable that a number of the dividing point is four.

A preferable example of the appliance to be implanted may be represented by an artificial blood vessel.

A form of an appliance to be implanted for realizing the above method of collapsing the appliance to be implanted may be represented by the appliance to be implanted which has an arrangement that each of the wire rings is collapsed into a wavy shape with having forwardly directed peaks and bottoms of forwardly directed valleys continuously and alternatively and which can be transported by being hauled forward with this condition kept wherein a front hooking portion for hauling the appliance to be implanted is provided at a general-midpoint between the peak and the bottom of the adjacent valley on the front end portion of the appliance to be implanted.

More concretely, it may be represented by an appliance to be implanted having an arrangement that front hooking portions for hauling the appliance to be implanted are provided at positions each of which locates at a general-midpoint between a dividing point and an adjacent dividing point wherein the dividing points divide the circumference of the front end portion into four segments and that rear hooking portions for hauling the appliance to be implanted are provided at four positions on the rear end portion of the appliance to be implanted wherein each of the four positions has the same phase as that of the front hooking portion, or an appliance to be implanted having an arrangement that front hooking portions for hauling the appliance to be implanted are provided at positions each of which locates at a general-midpoint between a dividing point and an adjacent dividing point wherein the dividing points divide the circumference of the front end portion into four segments and that rear hooking portions for hauling the appliance to be implanted are provided at two positions on circumference of the rear end portion of the appliance to be implanted or adjacent the two positions wherein each of the two positions locates at the bottoms of forwardly directed valleys.

In order to facilitate use at a site where appliance to be implanted is actually used it is preferable that front hooking portions for hauling the appliance to be implanted are provided at positions each of which locates at a general-midpoint between a dividing point and an adjacent dividing point wherein the dividing points divide the circumference of the front end portion into four segments and a transporting device wherein a wire passes into a tube and a front portion of the wire is selectively exposed through an opening portion provided on the tube is detachably be attached to the front hooking portions by engaging the tube and the wire.

With the same purpose, it is preferable that front hooking portions for hauling the appliance to be implanted are provided at positions each of which locates at a general-midpoint between a dividing point and an adjacent dividing point wherein the dividing points divide the circumference of the front end portion into an even number over four segments and the front portion is collapsed into a wavy shape with every other dividing point forming a forwardly directed peak and the adjacent dividing point forming a bottom of a forwardly directed valley and other intermediate wire ring and the rear end wire ring are collapsed into a wavy shape having the same phase as that of the front end portion and the appliance to be implanted is kept in a collapsed condition by a releasable retaining means with the above condition kept.

A concrete embodiment of the retaining means may be represented by a retaining means which is so arranged to release the appliance to be implanted from a collapsed condition by drawing a part of the retaining means out of the retaining means.

More concretely, it is effective if the retaining means comprises a string having a loop at one portion thereof and a retaining rod which is to pass through the loop of the string and the appliance to be implanted is kept in a collapsed condition with the retaining rod passing through the loop of the string and the appliance to be implanted is released from the collapsed condition by drawing the retaining rod out of the loop.

In this case also it is preferable that the intermediate wire ring is fixed to the tubular cover at positions which generally correspond to the positions where the front hooking portions are provided in order to effectively prevent the appliance to be implanted from being bulky.

A concrete position for providing the rear hooking portions for hauling the appliance to be implanted may be represented by positions which have the same phase as that of the front hooking portion provided at the front end portion of the appliance to be implanted on the rear end portion of the appliance to be implanted so as to make a number of the rear hooking portion equal to that of the front hooking portion, or every other positions which have the same phase as that of the front hooking portion provided at the front end portion of the appliance to be implanted on the rear end portion of the appliance to be implanted so as to make a number of the rear hooking portion half the number of the front hooking portion.

In this case also for collapsing the appliance to be implanted into a small size easily it is preferable that at least each of the front end wire ring and the rear end wire ring is connected with the tubular cover through a film member so that each of the front end wire ring and the rear end wire ring can make a back and forth movement relative to the tubular cover within a certain range and an annular gap formed between the front end wire ring and the tubular cover or between the rear end wire ring and the tubular cover is liquid-tightly sealed.

A preferable embodiment may be represented by that a number of the dividing point is four.

The present claimed invention is effective if applied to an artificial blood vessel which is one of the appliances to be implanted.

With the method of collapsing the appliance to be implanted in accordance with the present claimed invention, if a number of the front hooking portion is increased, the appliance to be implanted can be collapsed without increasing a number of the dividing point, in other words, a number of the peak or the bottom of the valley which is formed when collapsed. More specifically, if the appliance to be implanted is collapsed in a condition that the front hooking portion locates at a position of the peak, a number of the dividing point is required to be twice as many as the number of the front hooking portion. However, in accordance with the present claimed invention, the appliance to be implanted can be collapsed appropriately even though the number of the dividing point is equal to the number of the hooking portion. As a result, the appliance to be implanted can be kept in a collapsed condition so as not to be bulky without increasing a number of the dividing point. Further, with this arrangement, the appliance to be implanted can be hauled at a relatively straight portion between the peak and the valley of the front end wire ring locating at the front end portion of the appliance to be implanted. As a result, there is no chance that force is applied to a bent portion locally, which effectively avoids inconvenience that the wire rings are prevented from being restored into an appropriate original shape due to a possible habit of the wire rings because force is concentrated on the bent portion.

In addition, if the intermediate wire ring is fixed to the tubular cover at position which generally correspond to the positions where the front hooking portions are provided, when the intermediate wire ring is collapsed into a wavy shape having a peak and a valley, a generally mid-position between the peak and the valley of the intermediate wire ring, in other word a position which hardly move toward front and rear is fixed to the tubular cover. As a result, the appliance to be implanted can be transformed without dragging the tubular cover, resulting in a compact collapsed state of the appliance to be implanted.

Further, with the method of collapsing the appliance to be implanted in accordance with the invention, the appliance is hauled forward at the front hooking portions provided at generally mid-positions between the peak and the valley. However, the appliance does not tend to transform into a bulky shape that the mid-position where the front hooking portion is provided becomes a peak so as to double the number of the dividing points if the appliance to be implanted is once contained in the catheter in a collapsed condition. If, however, the appliance to be implanted is collapsed into a small size by the above retaining means, the appliance to be implanted can be prevented from being deformed during transportation without fail. If the appliance to be implanted is collapsed in advance by the use of the retaining means, there will be no need of collapsing the appliance to be implanted every time it is used, which makes it possible to introduce the appliance to be implanted into the catheter speedy.

In this case, if the retaining means comprises a string and a retaining rod wherein a retaining condition by means of the string can be released by a step of drawing the retaining rod, the appliance to be implanted can surely be operated to release the retaining means at a remote place after transported into a target position.

In addition, in case that the appliance to be implanted has a rear hooking portion for hauling the appliance to be implanted at a position which has generally the same phase as that of the front hooking portion on a rear end portion of the appliance to be implanted and the appliance to be implanted is collapsed so that the rear hooking portion locates at midpoints between the forwardly directed peaks and the bottoms of forwardly directed valleys, force can be applied uniformly to the rear end portion as well as the front end portion of the appliance to be implanted. As a result, the appliance to be implanted can be hauled appropriately.

In case that the appliance to be implanted has a rear hooking portion for hauling the appliance to be implanted at every other position which has generally the same phase as that of the dividing points on a rear end portion of the appliance to be implanted and the appliance to be implanted is collapsed so that the rear hooking portion locates at the bottoms of the forwardly directed valleys of the rear end portion, it is possible to haul the appliance to be implanted with occupying an opening of the rear end portion of the appliance to be implanted as less as possible. As a result, enough space can be secured for a transporting device which will be described later or other devices to be inserted into the appliance to be implanted from a rear end thereof.

If the front and rear end wire rings are connected with the tubular cover through a film member so that an annular gap formed between each of the front and rear end wire rings and the tubular cover is liquid-tightly sealed, a bent portion of the front and rear end wire rings can make a back and forth movement relative to the tubular cover. As a result, the tubular cover does not have to follow transformation of the front and rear end wire rings completely, thereby to make a range in which the tubular cover is bent smaller than that of the wire rings and to avoid forming a big wrinkle when folded. As a result of this, the appliance to be implanted can be collapsed in a compact state. In addition, since the tubular cover is not dragged much when released at a target position in a blood vessel, it can be restored into an original shape smoothly.

If a number of the dividing point is set to be four, the front hooking portions are arranged at four points each makes a right angle. As a result, the appliance to be implanted can be transported without applying force to the circumference of the front end portion thereof locally and can keep in an appropriate posture without inconvenience that the front end wire ring is tilted due to blood flow when released from the catheter at the target.

The above method can be extremely useful if applied to an artificial blood vessel which is required to be restored into an original shape at an affected portion in which an aneurysm or the like is present after being transported through a catheter in a collapsed compact condition.

If the appliance to be implanted is made to be collapsible by the above method of collapsing an appliance to be implanted, above-mentioned various effects can be produced.

In addition, if a transporting device comprising a tube and a wire is detachably attached to the appliance to be implanted, it can save time and effort for a user to set the transporting device on the appliance to be implanted every time the user uses the appliance to be implanted, which makes it possible to insert the appliance to be implanted into a catheter on the spot by the use of the transporting device.

BRIEF DESCRIPTION OF THE DRAWINGS

FIG. 6 is a schematic diagram showing the transporting device used in the embodiment.

FIG. 7 is a schematic diagram showing a hauling device used in the embodiment.

FIG. 8 is a perspective view showing a step to introduce the artificial blood vessel into the catheter by the use of forceps in the embodiment.

FIG. 9 is a perspective view showing a method of introducing the artificial blood vessel into a funneled tube by the use of the forceps in the embodiment.

FIG. 10 is an explanatory view showing the artificial blood vessel being folded in the funneled tube.

FIG. 15 is a perspective view showing a modification of the artificial blood vessel in accordance with the invention.

FIG. 16 is a perspective view of the collapsing device in a condition of being spread in accordance with a second embodiment of the invention.

FIG. 17 is a perspective view of the collapsing device in a condition prior to being used.

FIG. 18 is a view for explaining a procedure to collapse the artificial blood vessel with the collapsing device.

FIG. 19 is a view for explaining the procedure to collapse the artificial blood vessel with the collapsing device.

BEST MODES OF EMBODYING THE INVENTION

The invention will be described in detail with reference to embodiments thereof shown in the accompanying drawings.

First Embodiment

Figure 1:
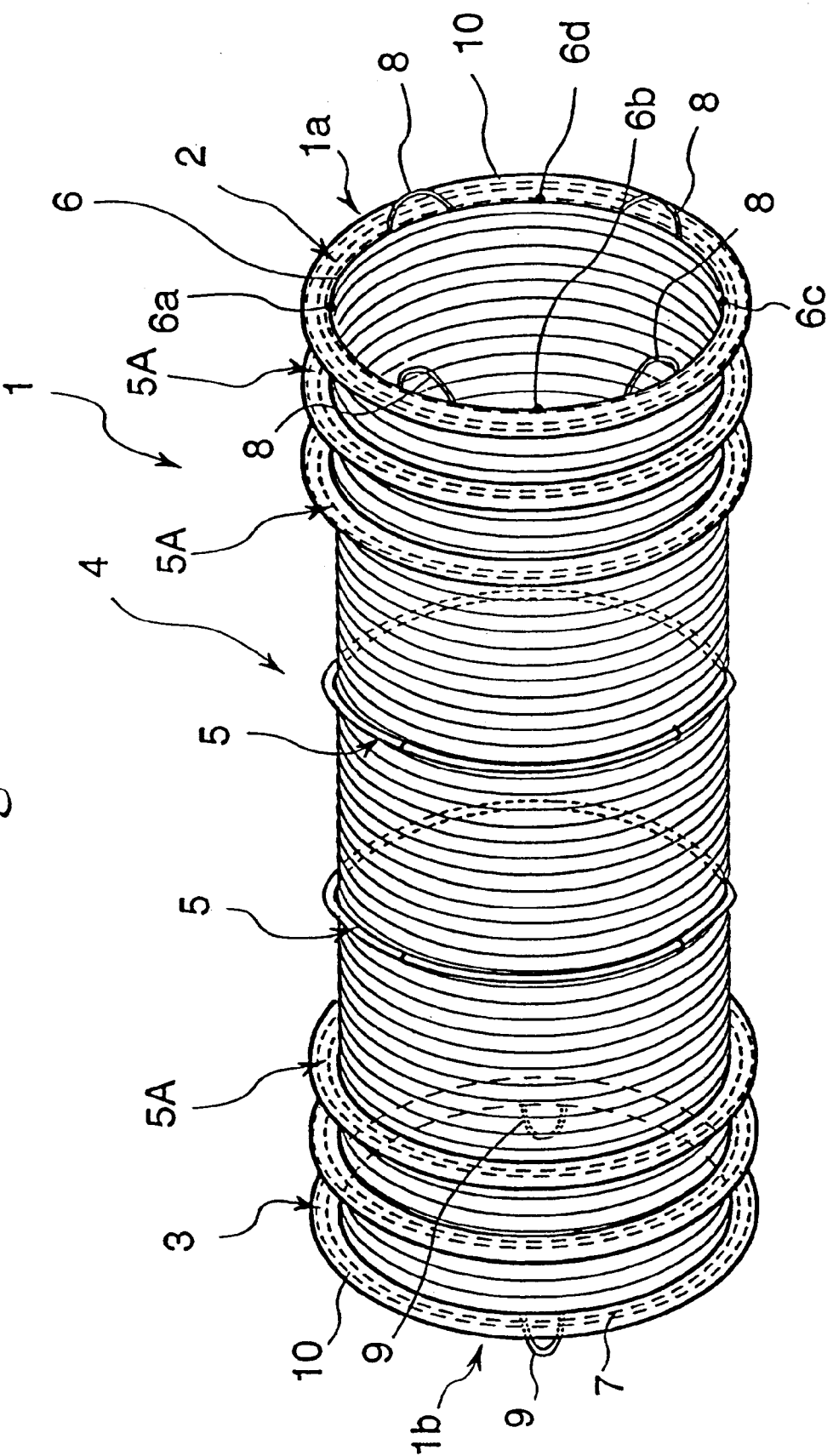
FIG. 1 is a perspective view of an artificial blood vessel in accordance with a first embodiment of the invention.

FIG. 1 shows an artificial blood vessel 1 as an appliance to be implanted in a condition before it is collapsed.

A fundamental arrangement of the artificial blood vessel 1 is described in documents such as the above-described document (PCT/JP96/01347 (International Laid Open Number WO96/36387)) which has been disclosed by the inventor of this invention. A fundamental arrangement of this embodiment will now be described according to the document A. The artificial blood vessel 1 comprises, as shown in FIG. 1, a front end wire ring 2, a rear end wire ring 3 arranged facing to the front end wire ring 2, a tubular cover 4 which connects the front end wire ring 2 and the rear end wire ring 3, and intermediate wire rings 5 arranged between the front end wire ring 2 and the rear end wire ring 3 and each of the wire rings 3, 4, 5 is given flexibly foldable elasticity.

In this embodiment, wires mainly made of material having a high resilient restoring force such as Ti—Ni alloy are referred to as a wire ring.

More concretely, the tubular cover 4 as shown in FIG. 1, consists of a flexible, tensile sheet shaped into a tube of bellows, the normal diameter of which generally corresponds to the shape of a portion of the human blood vessel at which the artificial blood vessel 1 is to be implanted. The sheet of the tubular cover 4 is, for example, of warps extending in the axial direction of the artificial blood vessel 1 woven with wefts extending in the circumferential direction thereof, wherein the warps are of mono-filament made of polyester (about 15 denier) and the wefts are of multi-filament made of a plurality of superfine filaments (about 50 denier) interwoven. The wefts are additionally woven with thread of polyethylene of about 10 denier to make the sheet of the tubular cover 4 thinner and stronger. The tubular cover 4 is coated, if necessary, with waterproof material, for example, collagen or albumin, to prevent leakage of blood.

Figure 2:
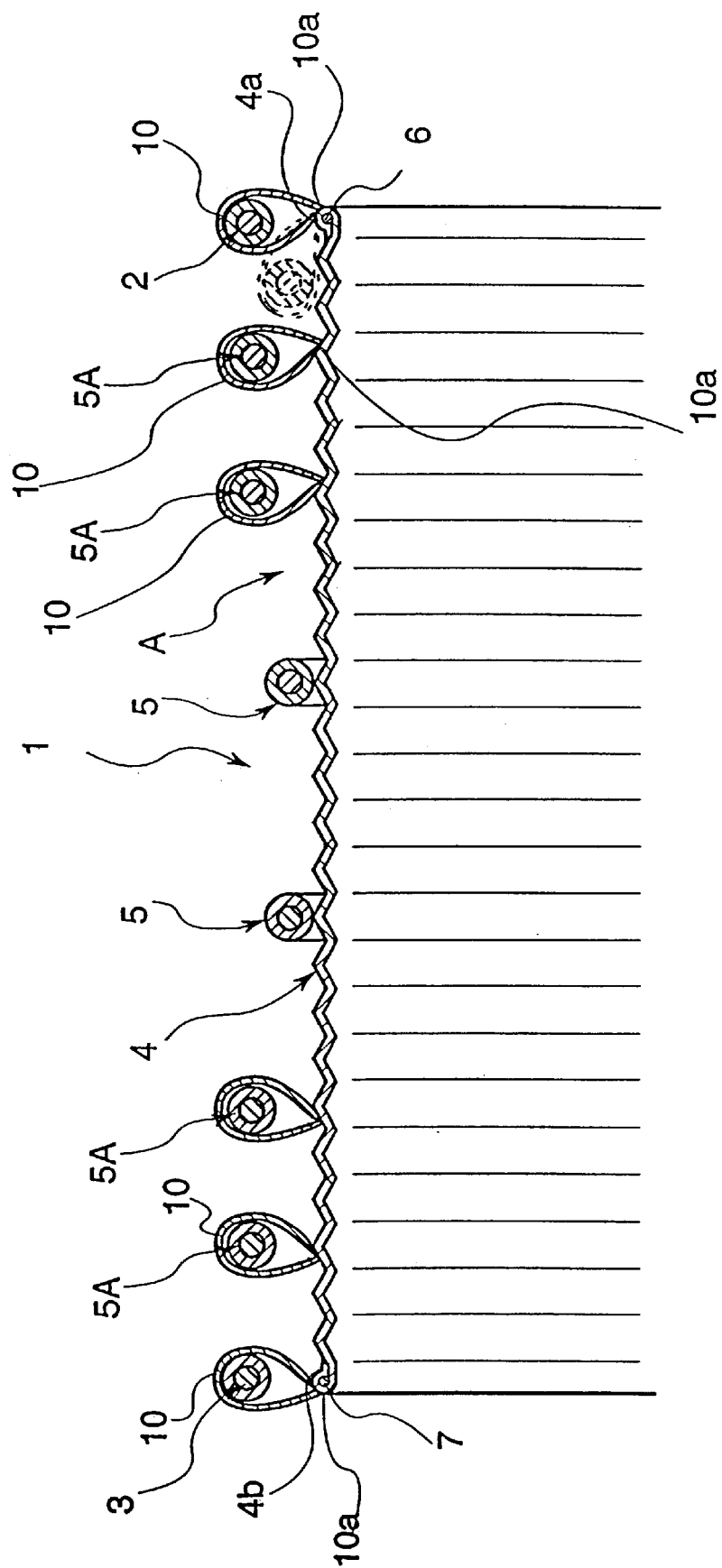
FIG. 2 is a partial cross-sectional view of the artificial blood vessel of the embodiment.

In addition, as shown in FIG. 2, auxiliary front and rear end wire rings 6, 7 are fixed to the tubular cover 4 by suturing or with adhesive at positions of the front and rear ends 4a, 4b which correspond to positions at which the front and rear end wire rings 2, 3 are fixed to the tubular cover 4. The auxiliary front and rear end wire rings 6, 7 are made of a wire which is thinner than that constitutes the front and rear end wire rings 2, 3. The auxiliary front and rear end wire rings 6, 7 give the artificial blood vessel 1 restoring force and attachability to a body where the artificial blood vessel 1 is to be implanted. As shown in FIG. 1, loop-shaped front hooking portions 8 are formed at four points each of which is a mid-point between the dividing points 6a, 6b, 6c, 6d and the adjacent dividing points 6b, 6c, 6d, 6a each of which equally quadrisects the circumference of the auxiliary front end wire ring 6.

In addition, loop-shaped rear hooking portions 9 are formed at two positions on generatrices which pass through every other dividing points 6b, 6d.

The hooking portions 8, 9 in accordance with the embodiment are formed of string. It may not necessarily be of string, but a hole directly formed on the tubular cover 4 may be utilized as the hooking portions, if there is no trouble.

The front and rear end wire rings 2, 3 are axially spaced apart and arranged face to face and an inner diameter of them is set to be a little larger than that of the above-mentioned cover 4. The front and rear end wire rings 2, 3 are put in a bag-shaped film member 10 which is mounted on the front end 4a or the rear end 4b of the tubular cover 4 so as to make a back and forth movement relative to the tubular cover as shown. in FIG. 2.

The film member 10 is bag-shaped in which whole of each of the front and rear end wire rings 2, 3 wrapped up and an inner end 10a of the film member 10 is attached to the tubular cover 4 almost to surround the outer circumference thereof with thread or by adhesive so as to allow each of the front and rear end wire rings 2, 3 to make a back and forth movement by making use of transformation of the film member 10 and to liquid-tightly seal a ring-shaped gap between the front and rear end wire rings 2, 3 and the tubular cover 4.

The film member 10 used in this embodiment is made of the same material as that of the sheet which constitutes the tubular cover 4.

A plurality of intermediate wire rings 5 have an arrangement of being wrapped with protective film such as cloth or braid members like the above-mentioned front and rear end wire rings 2, 3 and are arranged general-equidistantly spaced apart between the front and rear end wire rings 2, 3. Each of the intermediate wire rings 5 is fixed to the tubular cover 4 at four positions whose each phase is the same as that of the front hooking portions 8 on the circumference thereof with thread, by adhesive or the like and help keep the tubular shape of the tubular cover 4 together with the above-mentioned front and rear end wire rings 2, 3.

In this embodiment each two of the intermediate end wire rings 5A arranged near the front and rear end wire rings 2, 3 are set to have a larger inner diameter than the outer diameter of the tubular cover 4 and wrapped in a bag-shaped film member 10 so as to allow a back and forth movement relative to the tubular cover 4 like the front and rear end wire rings 2, 3. The film member 10 is attached to the tubular cover 4 at one end thereof almost to surround the outer circumference thereof with thread or by adhesive so as to allow each of the intermediate end wire rings 5A to make a back and forth movement through the film member and to liquid-tightly seal a ring-shaped gap between the intermediate end wire ring 5A and the tubular cover 4.

The artificial blood vessel 1 is introduced in order to prevent blood flowing into aneurysm by being implanted into a portion, for example, where aneurysm is caused.

Figure 12:
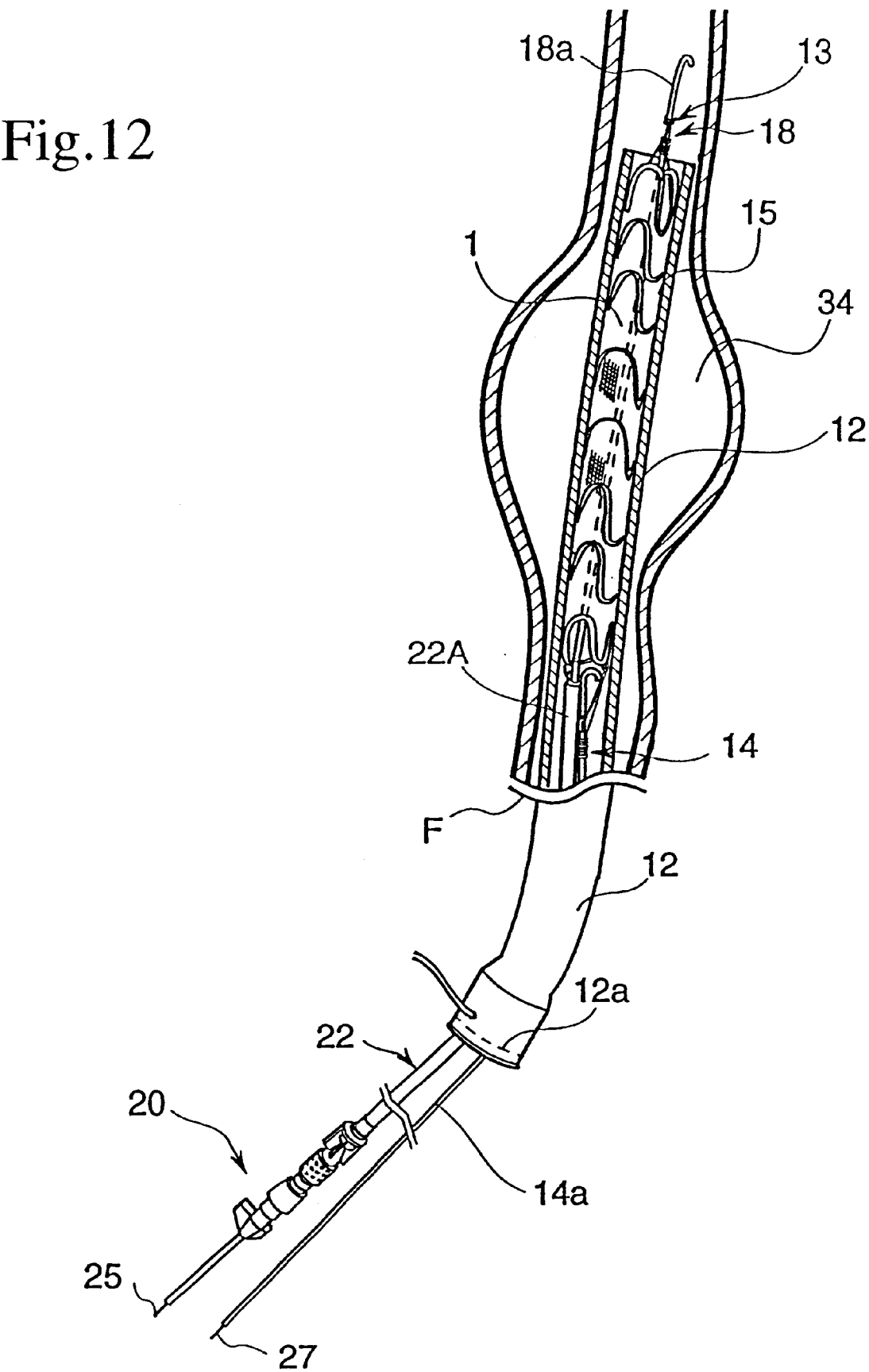
FIG. 12 shows a step to implant the artificial blood vessel of the embodiment into a target position.

For introducing the artificial blood vessel 1, a following transvascular method-is adopted; the artificial blood vessel 1 is first put in a catheter 12 (see FIG. 14) in a collapsed condition, the catheter 12 is inserted into, for example, a groin of a thigh, the catheter 12 is transported to a target position as shown in FIG. 12 by the use of a transporting device 13 shown in FIG. 3 through FIG. 6, the artificial blood vessel 1 is released from the catheter 12, the artificial blood vessel 1 is adjusted to be placed at an appropriate position by being hauled rearward by the use of a hauling device 14 shown in FIG. 7, FIG. 12 through FIG. 14, if necessary, and then the artificial blood vessel 1 is released from a condition of being collapsed so as to be restored into a predetermined shape.

The transporting device 13 comprises, as shown in FIG. 3 through FIG. 6, an operating rod 18 which is flexible and made of metal and which can integrally be transported with the artificial blood vessel 1 and detachably be attached to the artificial blood vessel 1, an opening portion 23 formed near the front end of the operating rod 18 and four pieces of strings 24 having both their ends fixed to the operating rod 18 near the opening portion 23 by a fixing rope 36 and their middle portions formed into loops to be looped portions 24a.

Figure 3:
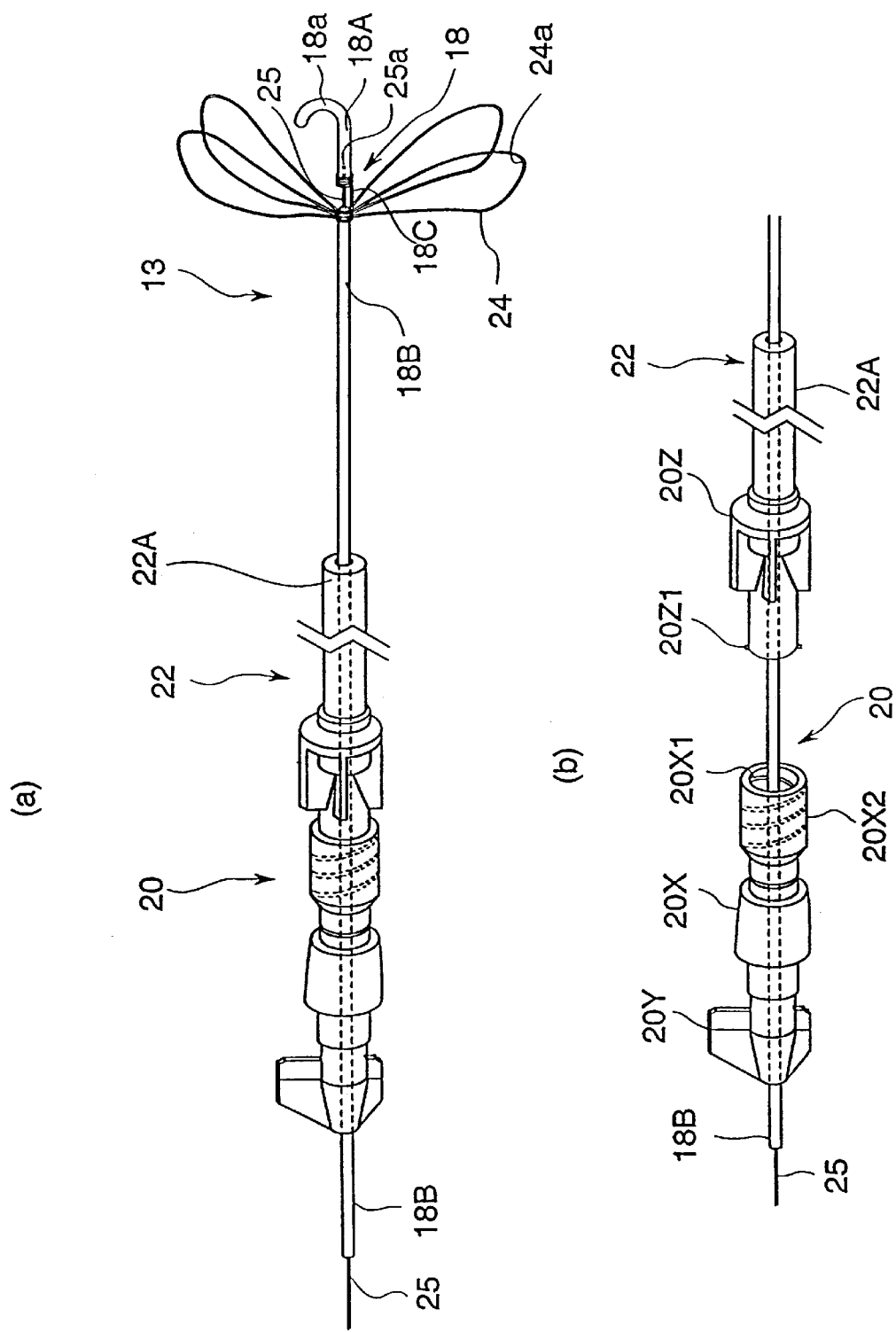
FIGS. 3(a), (b) is a schematically shown perspective view of a transporting device used in the embodiment.

More concretely, the operating rod 18 comprises, as shown in FIG. 3 though FIG. 6, a flexible metallic tube element 18A whose front end portion is connected to a helical spring for guiding, a tube element 18B whose base end portion is connected to the helical spring for guiding, a tube connecting element 18C which connects outer circumferences of the tube elements 18A, 18B with the opening portion 23 formed therebetween and a wire 25 which can be inserted into inside of the tube elements 18A and 18B movably and longitudinally. Each of the tube elements 18A and 18B is fixed to the tube connecting element 18C by means of the fixing ropes 36, 37. Needless to say, each of the tube elements 18A and 18B may be fixed by means of another means other than the fixing ropes 36, 37. A balloon catheter 22 is attached to the tube element 18B through a rock mechanism 20.

The artificial blood vessel 1 can be engaged with the transporting device 13 so as to be integrally transported with the transporting device 13 by following steps; a front tip 25a of a wire 25 is exposed from the opening portion 23 by moving the wire 25 longitudinally relative to the tube elements 18A, 18B, the string 24 is engaged with the front hooking portion 8 of the artificial blood vessel 1, the loop 24a of the string 24 is engaged with the front tip 25a of the wire 25 and the front tip 25a is drawn into the tube element 18A locating a front side through the opening portion 23.

The tube connecting element 18C consists of three cylindrical bodies, each of which is arranged along the outer circumference of the tube elements 18A, 18B, wherein one cylindrical body locating the center is made longer than the other cylindrical bodies so as to project from the other cylindrical bodies longitudinally.

The balloon catheter 22 comprises a pipe-shaped body 22A, a balloon portion (not shown in drawings) which is provided at a front tip 22a of the body 22A and can expand by introducing air thereinto if necessary and an inlet (not shown in drawings) which is provided at a base end of the body 22A and which is for introducing air into the balloon portion through the body 22A. Inside the body 22A the tube element 18B passes through longitudinally and movably and near the base end of the body 22A provided is a lock mechanism 20.

The lock mechanism 20 is, as shown in FIG. 3(*a*), to alternatively lock the tube element 18B locating at the base end of the transporting device 13 and the balloon catheter 22. FIG. 3(*b*) shows a condition wherein the lock mechanism 20 is released from a condition of being locked. The lock mechanism 20 comprises a body portion 20X which can be fixed to the outer circumference of the tube element 18B by the use of a knob 20Y and a lure lock portion 20Z which is provided at a base end of the balloon catheter 22. At the front tip of the body portion 20X formed is a receiving portion 20X2 having a helical groove 20X1 at an inner face thereof, while at an outer face of the lure lock portion 20Z corresponding to the receiving portion 20X2 formed is a projection 20Z1 which is helically connected with the helical groove 20X1 alternatively. Thus the balloon catheter 22 can be connected with the tube element 18B by helically connecting the projection 20Z1 with the helical groove 20X1. If the projection 20Z1 of the lure lock portion 20Z is released from the helical groove 20X1, the balloon catheter 22 alone can be advanced with the tube element 18B left where it is.

The hauling device 14 has, as shown in FIG. 7, the same arrangement as that of the transporting device 13 except that a number of a string 29 is two so as to correspond with a number of the rear hooking portion 9 of the artificial blood vessel 1 and that it has not any auxiliary operating rod.

More concretely, the hauling device 14 is so arranged that a wire 27 is contained in a tube 26. The wire 27 which is drawn out of an opening portion 28 provided on the tube 26 makes an engagement with a rear hooking portion 9 provided on one part of the auxiliary rear end wire ring 7 locating rear and then the wire 27 is drawn into the tube 26 again so as to hold and make an engagement with the auxiliary rear end wire ring 7. The hauling device 14 can haul the artificial blood vessel 1 toward an opposite direction to a direction that the transporting device 13 does.

Next, a process of collapsing the artificial blood vessel 1 having the above arrangement will be explained.

Figure 4:
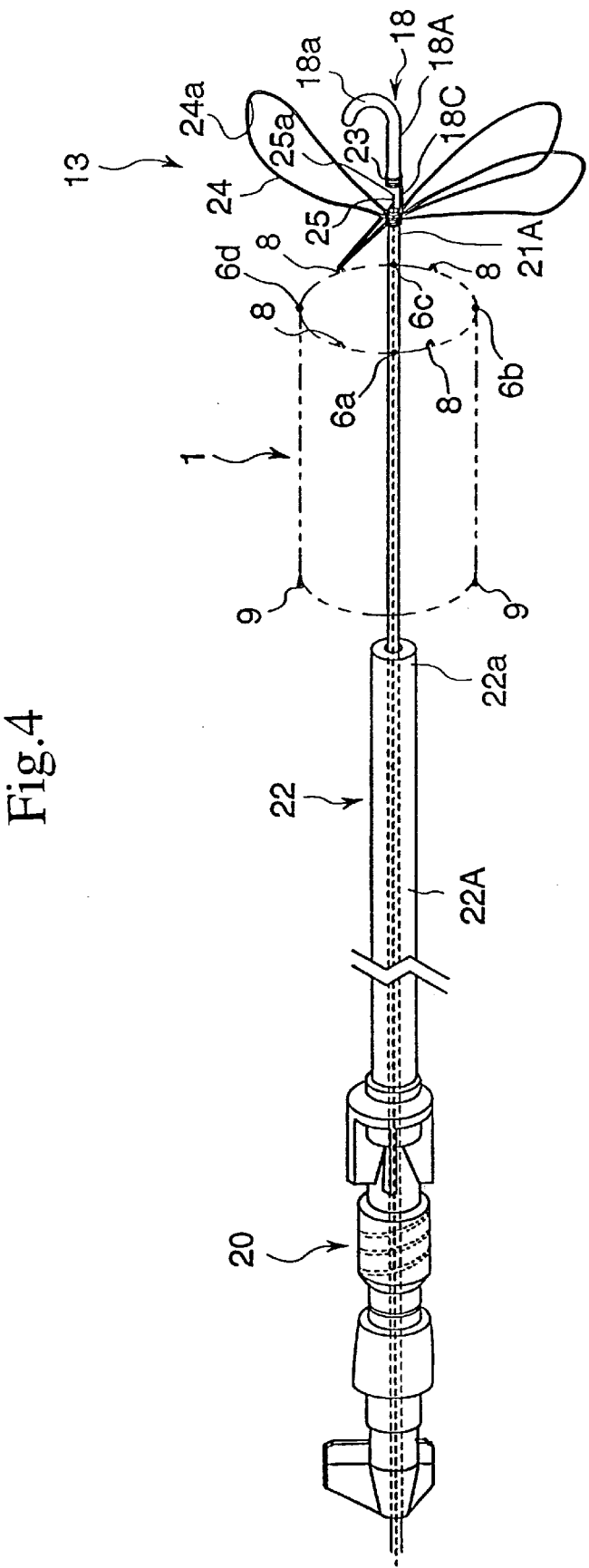
FIG. 4 is a schematically shown perspective view of the transporting device and the artificial blood vessel.
Figure 5:
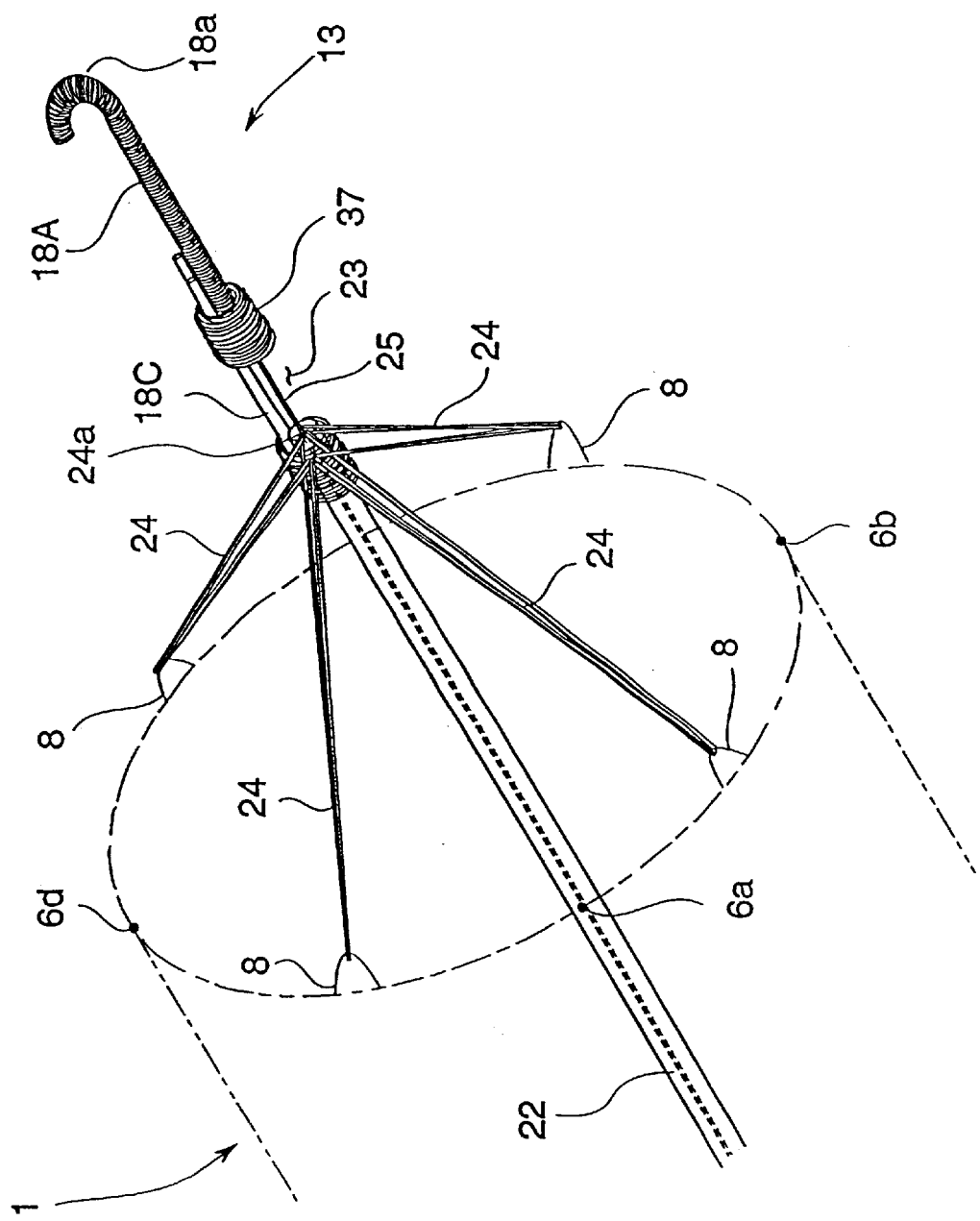
FIG. 5 is a magnified perspective view showing a part of the transporting device.
Figure 11:
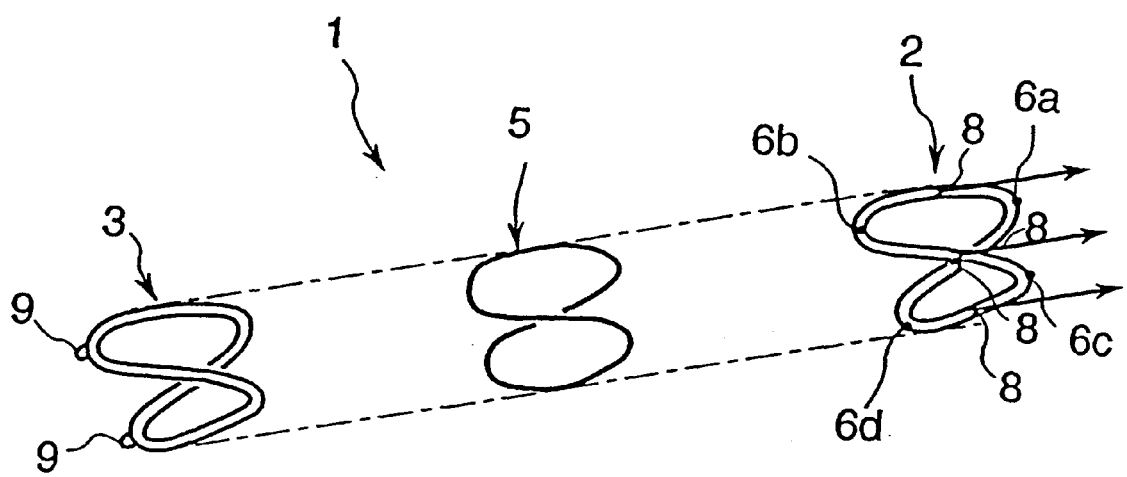
FIG. 11 is a schematic diagram showing each of wire rings being folded.

First, lock the lock mechanism 20 and then insert the transporting device 13 into the artificial blood vessel 1 in a condition wherein the operating rod 18 and the balloon catheter 22 are made to transport integrally. Pass each of the four strings 24 respectively through the looped front hooking portions 8 each of which is provided on a mid-position between the dividing point 6a, 6b, 6c, 6d and the dividing point 6b, 6c, 6d, 6a of the artificial blood vessel 1 and then, as shown in FIG. 4, engage each of the loops 24a of the strings 24 with the front tip 25a of the wire 25 exposed out of the opening portion 23 of the transporting device 13 one by one. Then engage the artificial blood vessel 1 with the transporting device 13 through the front hooking portions 8 and the strings 24 in a condition that the artificial blood vessel 1 fits over the transporting device 13, as shown in FIG. 5, by pushing the front tip 25a of the wire 25 into the tube element 18A of the operating rod 18 again. At this time the front tip 22a of the balloon catheter 22 locates at a position a little closer to a base side than the rear end of the artificial blood vessel 1 as shown in FIG. 4. If the balloon catheter 22 locates inside of the artificial blood vessel 1, the artificial blood vessel 1 cannot be collapsed into a small size due to the balloon catheter 22.

Next, as shown in FIG. 7, like the transporting device 13 the hauling device 14 is inserted into the artificial blood vessel 1 and with keeping the condition each of the two strings 29 is passed through the rear hooking portion 9 of the artificial blood vessel 1 so that the hauling device 14 engages the artificial blood vessel 1.

Then, as shown in FIG. 8 through FIG. 10, the artificial blood vessel 1 is inserted into the cartridge 31 though the funneled tube 30 and with the forceps 33. In this embodiment the artificial blood vessel 1 is inserted into the cartridge 31 using the forceps 33, however, the artificial blood vessel 1 may be folded into an appropriate wavy shape and inserted into the cartridge by hand without using any forceps. A concrete method for inserting the artificial blood vessel 1 by the use of the forceps will now be explained.

First, insert the front tip of the artificial blood vessel 1 into the funneled tube 30 with the forceps 33 put along the generatrices each of which passes through the two dividing points (for example, 6a and 6c) each facing across the axis so as to make the dividing points 6a and 6c form the forwardly directed peaks as shown in FIG. 8. Then the auxiliary front end wire ring 6 of the artificial blood vessel 1 is deformed to be flat with the positions picked up by the forceps 33, namely, with the dividing points 6a and 6c approaching toward each other to be pushed into the cartridge 31 while the other dividing points 6b and 6d are restrained from the movement by sliding contact with the tapered inner surface of the funneled tube 30. When the auxiliary front end wire ring 6 reaches adjacent one end 31a of the cartridge 31, the auxiliary front end wire ring 6 as a whole is folded into a regular wavy shape with the dividing points 6a, 6c forming forwardly directed peaks and other dividing points 6b, 6d forming the bottoms of forwardly directed valleys. Other wire rings 2, 3, 5, 5A, 7 are collapsed into a small size to take a wavy shape having the same phase as that of the auxiliary front end wire ring 6. In this case, four front hooking portions 8 formed at mid-positions between the dividing points 6a, 6b, 6c, 6d and the dividing points 6b, 6c, 6d, 6a locate at mid positions between the forwardly directed peaks and the bottoms of forwardly directed valleys. At this time, each of the front hooking portions 8 is held by and engaged with the transporting device 13 through the strings 24 as shown in FIGS. 9 and 10. It is effective if necessary that a string is introduced from a side of the cartridge 31 so as to pass through the front hooking portion 8 of the artificial blood vessel 1 and the artificial blood vessel 1 is drawn into the cartridge 31 by pulling the string.

Next, the artificial blood vessel 1 which has been collapsed into a small size as mentioned above is transported to a target organ in a body, namely an affected portion 34. In order to transport the artificial blood vessel 1, first, as shown in FIG. 12, introduce the catheter 12 which has a seal mechanism 12a at the base end thereof into a body through a coxal artery of the groin as far as the front portion of the catheter 12 is positioned adjacent the affected portion 34 such as an aneurysm of the aorta. Then connect the cartridge 31 liquid-tightly with the base end of the catheter 12 through the seal mechanism 12a by pushing a cap 31a which is attached to the cartridge 31 so as to be introduced into the catheter 12. Next, operate the transporting device 13 to push forward so as to move the collapsed artificial blood vessel 1 from the cartridge 31 to the catheter 12 and proceed the operation until it reaches the affected portion 34. This process is described in the pre-mentioned document {PCT/JP/01347(International Laid Open Number WO96/36387)}.

During this time the base of the balloon catheter 22 locating out of the body can be grasped to push forward the artificial blood vessel 1. The hauling device 14 follows a movement of the artificial blood vessel 1. The lock mechanism 20 provided at the base end of the balloon catheter 22 and the base end 14a of the hauling device 14 are kept to position out of the body through the seal mechanism 12a. While the lock mechanism 20 is locked, the balloon catheter 22 and the operating rod 18 are transported integrally. Therefore, a force applied to the base end of the balloon catheter 22 is directly transmitted to the front portion 18a of the operating rod 18.

Figure 13:
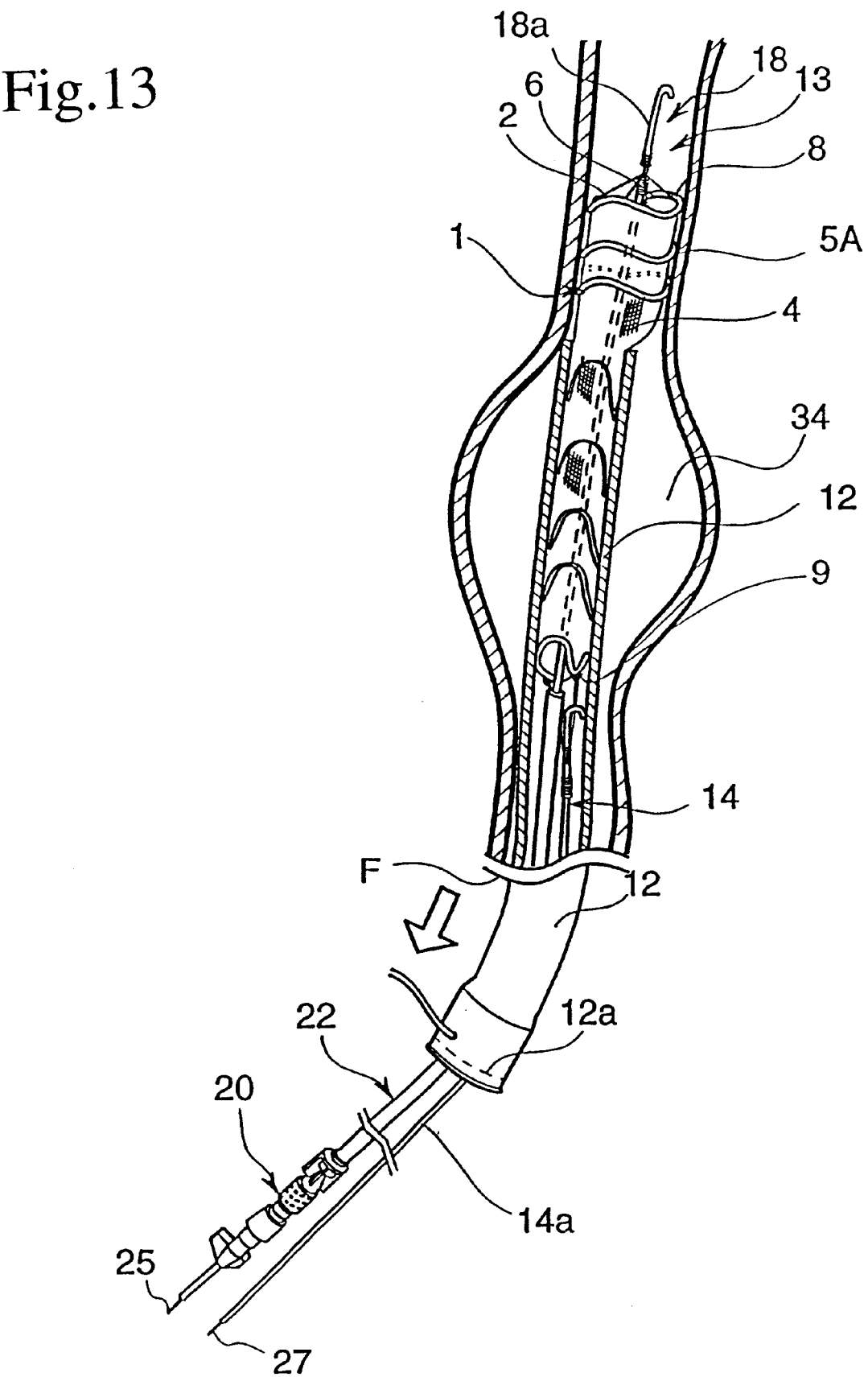
FIG. 13 shows a step to implant the artificial blood vessel of the embodiment into the target position.

After the artificial blood vessel 1 is arranged at the target position, the artificial blood vessel 1 is released from the catheter 12 as shown in FIGS. 12 and 13 by pulling the catheter 12 backward with the artificial blood vessel 1 kept at the position by the transporting device 13. Prior to or after this procedure, the artificial blood vessel 1 can be pulled backward so as to adjust the position by the use of the hauling device 14, if necessary.

Figure 14:
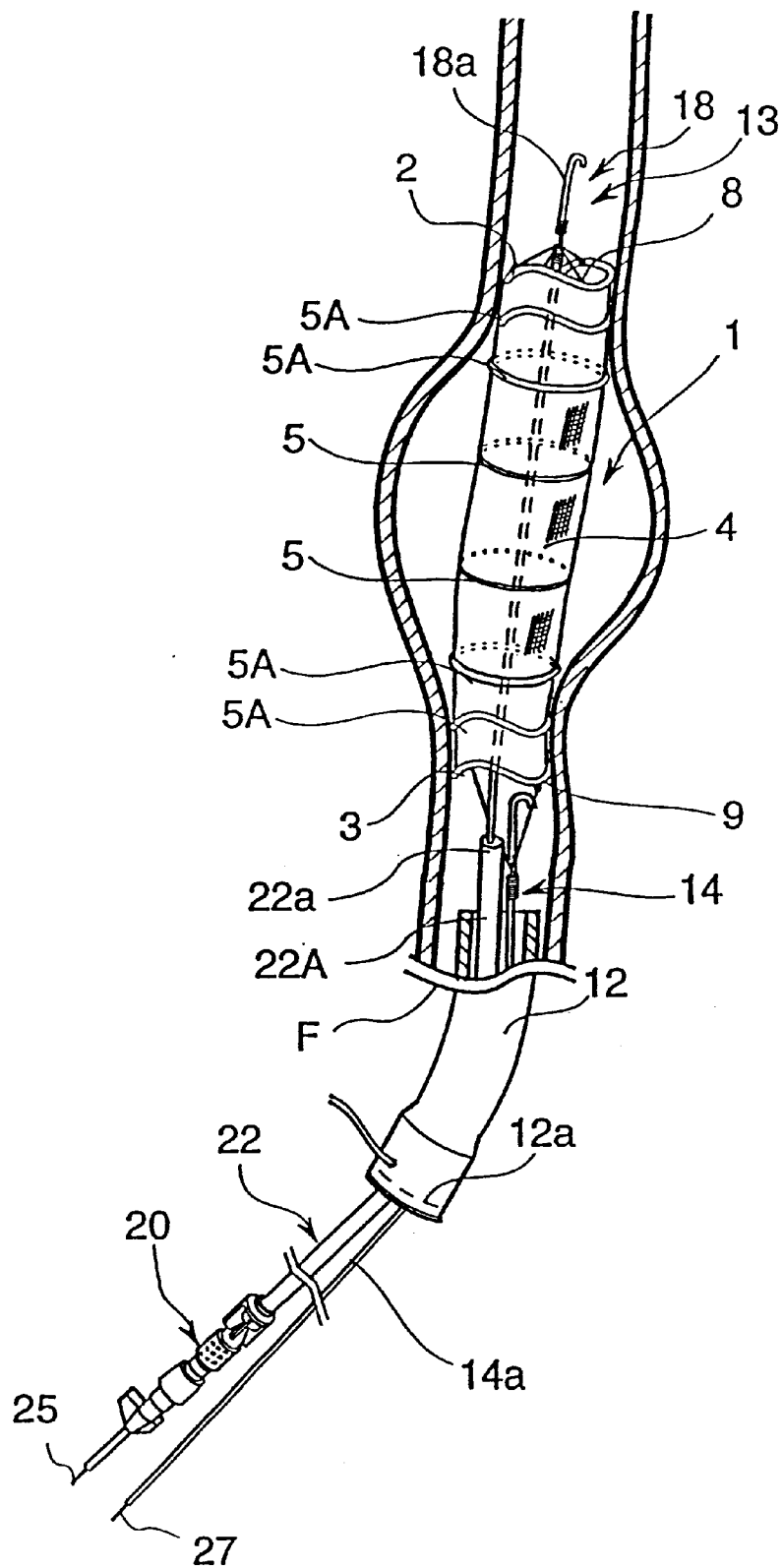
FIG. 14 shows a step to implant the artificial blood vessel of the embodiment into the target position.

FIG. 14 shows a state in which the artificial blood vessel 1 is tightly attached to the blood vessel. A state in which each of the ring members 2, 3, 5, 5A, 6 is not restored into a shape of round is due to pulsations of the blood vessel to which movement of each of the ring members 2, 3, 5, 5A, 6 follows. After the artificial blood vessel 1 is arranged at the target position, the balloon catheter 22 is transported until the front tip 22a of the body 22A reaches the front end of the artificial blood vessel 1 and then the artificial blood vessel 1 may be restored into a shape of round completely by inflating a balloon portion of the balloon catheter 22, if necessary. Finally, take the transporting device 13 and the hauling device 14 out of the body by drawing the wire 25 from the base end 13a of the transporting device 13 and the wire 27 from the base end 14a of the hauling device 14 so as to release engagement of the transporting device 13 and the hauling device 14 with the artificial blood vessel 1. Then the artificial blood vessel 1 is completed to implant into the affected portion 34 as the target position.

As mentioned above, in this embodiment implantation of the artificial blood vessel 1 is completed and the artificial blood vessel 1 produces an effect of preventing occlusion of blood vessels of the affected portion 34.

With the method of collapsing the artificial blood vessel 1 in accordance with the first embodiment, even if a number of the front hooking portion 8 is increased, the artificial blood vessel 1 can be collapsed without increasing a number of the dividing point 6a, 6b, 6c, 6d, in other words, a number of the peak or the bottom of the valley which is formed when collapsed. More specifically, if the artificial blood vessel 1 is collapsed in a condition that the front hooking portion 8 locates at a position of the peak, a number of the dividing point 6a, 6b, 6c, 6d is required to be eight, namely, twice as many as the number of the front hooking portion 8. However, in accordance with the above method, the artificial blood vessel 1 can be collapsed appropriately even though the number of the dividing point 6a, 6b, 6c, 6d is four, namely, equal to the number of the hooking portion 8. As a result, although the number of the front hooking portion 8 is increased so that the front end portion of the artificial blood vessel 1 can be held at a plurality of positions to prevent the artificial blood vessel 1 from being tilted due to blood flow after released from the catheter 12, or to haul the artificial blood vessel 1 equally not to be tilted when transported, the artificial blood vessel 1 can be kept in a collapsed condition so as not to be bulky without increasing a number of the dividing point 6a, 6b, 6c, 6d. Especially since the artificial blood vessel 1 of this embodiment comprises the wire rings 2, 3, 5 and the tubular cover 4 alone and does not have any other structure element to backup whole of the artificial blood vessel, it is extremely effective to hold four positions of the artificial blood vessel 1 in order to keep it in a predetermined shape. In addition, with this arrangement, the artificial blood vessel 1 can be hauled at a relatively straight portion between the peak and the valley of the front end wire ring 2 locating at the front end portion of the artificial blood vessel 1. As a result, there is no chance that force is applied to a bent portion locally, which effectively avoids inconvenience that the front end wire ring 2 or the auxiliary front end wire ring 6 are prevented from being restored into an appropriate original shape due to a possible habit of the front end wire ring 2 or the auxiliary front end wire ring 6 because force is concentrated on the bent portion.

In addition, since the intermediate wire ring 5 is fixed to the tubular cover 4 at position which generally correspond to the positions where the front hooking portions 8 are provided, when the intermediate wire ring 5 is collapsed into a wavy shape having a peak and a valley, a generally mid-position between the peak and the valley of the intermediate wire ring 5, in other word, a position which hardly move toward front and rear is fixed to the tubular cover 4. As a result, the artificial blood vessel 1 can be transformed without dragging the tubular cover 4, resulting in a compact collapsed state of the artificial blood vessel 1.

Further since the front and rear end wire rings 2, 3 and the intermediate end wire ring 5A are connected with the tubular cover 4 through a film member 10 so that an annular gap formed between each of the front and rear end wire rings 2, 3 and the intermediate end wire ring 5A and the tubular cover 4 is liquid-tightly sealed, a bent portion of the front and rear end wire rings 2, 3 and the intermediate end wire ring 5A can move back and forth relative to the tubular cover 4. As a result, the tubular cover 4 does not have to follow transformation of the front and rear end wire rings 2, 3 or the intermediate end wire ring 5A completely, which allows the tubular cover 4 to bend less than the front and rear end wire rings 2, 3 or the intermediate end wire ring 5A, resulting in smooth restoration of the wire rings 2, 3, 5A.

Especially, since a number of the dividing point 6a, 6b, 6c, 6d is set to be four and the front hooking portions 8 are arranged at four points each making a right angle, the artificial blood vessel 1 can be transported without applying force to the circumference of thereof locally and can keep in an appropriate posture without being tilted when released from the catheter 12 at the target position.

Since the rear hooking portion 9 for hauling the artificial blood vessel 1 are provided at two portions, it is possible to haul the artificial blood vessel 1 with occupying an opening of the rear end portion of the artificial blood vessel 1 as less as possible. As a result, enough space can be secured for a transporting device 13 or other devices to be inserted into the artificial blood vessel 1 from a rear end thereof.

In addition, if the transporting device 13 comprising the operating rod 18 and the wire 25, as shown in FIG. 4, is detachably attached to the artificial blood vessel 1, it can save time and effort for a user to set the transporting device 13 on the artificial blood vessel 1 every time the user uses the artificial blood vessel 1, which makes it possible to insert the artificial blood vessel 1 into a catheter 12 on the spot by the use of the transporting device 13.

In addition, as described above, since the tube connecting element 18C comprises three cylindrical connecting bodies and the connecting body locating at the center is made longer than the other two connecting bodies, when the tube elements 18A and 18B are bent, an excessive force is not applied to a portion 18c connecting the connecting element 18C and the tube elements 18A and 18B and an elastic force of the tube connecting element 18C will vary smoothly along the longitudinal direction around the portion 18c, thereby to keep the tube elements 18A and 18B in a shape forming a natural curve.

The present claimed invention is not limited to the embodiment described above and there may be various modifications without departing from the spirit of the invention.

For example, in this embodiment, the number of the front hooking portion 8 is four and the number of the string 24 of the transporting device 13 is also four, however, the number of the string 24 is not necessarily be four as far as it is an even number.

Further, in this embodiment, the number of the rear hooking portion 9 is two and the number of the string 29 is also two. This is intended to utilize limited space effectively in the catheter 12. Therefore the number of the rear hooking portion 9 and the strings 29 may be four, as shown in FIG. 15, if there is enough space in the catheter 12 so that the force applied by the hauling device 14 is uniformly distributed to stabilize a state of hauling rearward. In this case, the rear hooking portion 9 is formed at the position which has the same phase as that of the front hooking portion 8.

In addition, in this embodiment, the intermediate wire rings 5 are fixed to the tubular cover 4 at four positions on the circumference thereof in order to lessen volume when collapsed, however, the intermediate wire rings 5 may be fixed to the tubular cover 4 all along the circumference thereof if there is enough space for the collapsed artificial blood vessel 1.

Further, the transporting device may comprise an operating rod and a wire alone which is to be passed through inside the operating rod and does not have any strings. In this case, the front hooking portion of the artificial blood vessel is formed to be big so as to engage the front hooking portion with the wire.

Second Embodiment

Next, a second embodiment of the invention will be explained with reference to FIG. 16 through FIG. 26.

Figure 24:
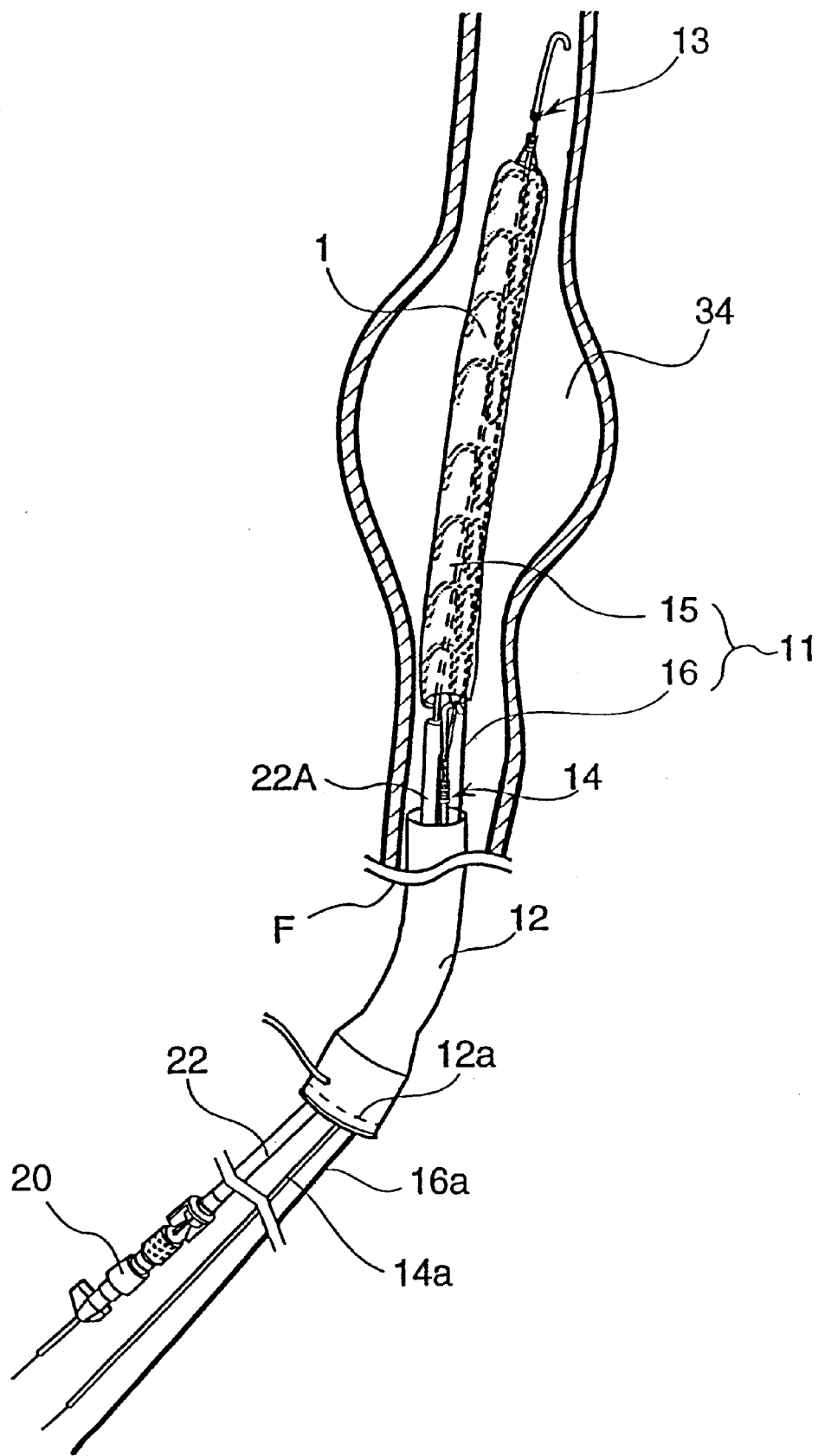
FIG. 24 is an explanatory view showing a step to implant the artificial blood vessel of the embodiment into a target position.

A fundamental arrangement of the artificial blood vessel 1 and a method of collapsing the artificial blood vessel 1 is generally the same as that of the above embodiment, except for the following; the artificial blood vessel 1 is kept in a collapsed condition by a retaining means 11 as shown in FIG. 24 during a process from introducing the artificial blood vessel 1 into the catheter 12 to releasing it from the catheter 12 at the target position and the artificial blood vessel 1 is released from a collapsed condition after released from the catheter 12.

Followings explained will be only the difference and common elements will be omitted to explain.

The retaining means 11 comprises a wrapping member 15 and a wire rod 16 which holds the wrapping member 15 in a shape of a tube.

More concretely, the wrapping member 15 is to wrap the artificial blood vessel 1, and interwoven with wefts and warps to form a mesh as shown in FIG. 16 so as to be expansible and generally flat when spread. The wefts and warps are interwoven at each points of intersection and stretching of a cross of the mesh formed at the intersection provides whole of the wrapping member 15 with stretching properties along lengthwise and crosswise directions.

The wire rod 16 is flexible made of nickel titanium alloys. The wire rod 16 holds the wrapping member 15 in a shape of a tube as shown in FIG. 17 by steps of overlapping both edges 15a, 15b of the wrapping member 15 so as to make the wrapping member 15 in a shape of a general tube and passing the wire rod 16 so as to sew the overlapped edges 15a, 15b in broken lines.

Then the artificial blood vessel 1 is contained in the wrapping member 15 of the retaining means 11 in a collapsed condition by the use of a tubular member 331 having a funneled tube 330 at one end thereof as shown in FIG. 18.

Figure 20:
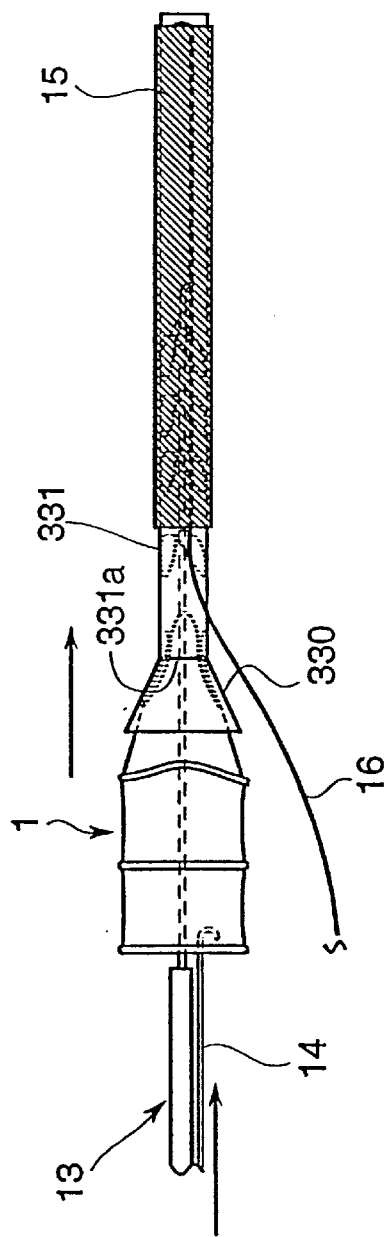
FIG. 20 is a view for explaining the procedure to collapse the artificial blood vessel with the collapsing device.

More specifically, fit the wrapping member 15 over the tubular member 331 from a front side of a guide member 332 which has a tapered face 332A at the front tip thereof and which is previously inserted into the tubular member 331, as shown in FIG. 18, with the wrapping member 15 kept in a tube shape by means of the wire rod 16 so as to cover the outer surface of the tubular member 331 as shown in FIG. 19. And then insert the collapsed artificial blood vessel 1 into the tubular member 331 from one end 331a of the tubular member 331 along a tapered face of the funneled tube 330 as shown in FIG. 20. The transporting device 13 is used in order to transport the artificial blood vessel 1 in the tubular member 331.

Like the first embodiment the artificial blood vessel 1 is also hauled forward by pulling the front side of the artificial blood vessel 1 by means of the transporting device 13 with the two points 6a, 6c each facing across the axis of the artificial blood vessel 1 out of the dividing points 6a, 6b, 6c, 6d of the artificial blood vessel 1 forming forwardly directed peaks. Then whole of the auxiliary front end wire ring 6 is collapsed into a small size to take a wavy shape with the dividing points 6a, 6c forming forwardly directed peaks and other dividing points 6b, 6d forming bottoms of forwardly directed valleys. Other wire rings 2, 3, 5, 5A, 7 are also collapsed into a small size to take a wavy shape having the same phase as that of the auxiliary front end wire ring 6. In this case, four front hooking portions 8 formed at mid-positions between the dividing points 6a, 6b, 6c, 6d and the dividing points 6b, 6c, 6d, 6a locate at mid positions between the forwardly directed peaks and the bottoms of forwardly directed valleys. As mentioned above, the artificial blood vessel 1 is inserted into the inner side of the cartridge 331 at a position corresponding to a position where the wrapping member 15 is mounted as shown in FIG. 20.

Figure 21:
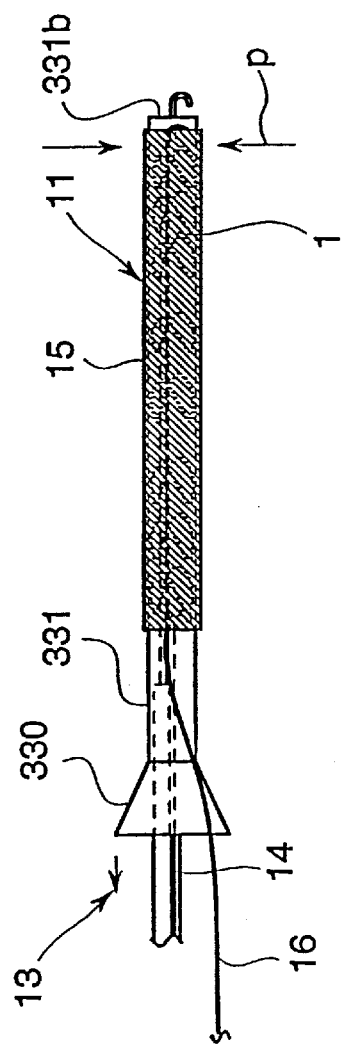
FIG. 21 is a view for explaining the procedure to collapse the artificial blood vessel with the collapsing device.
Figure 22:
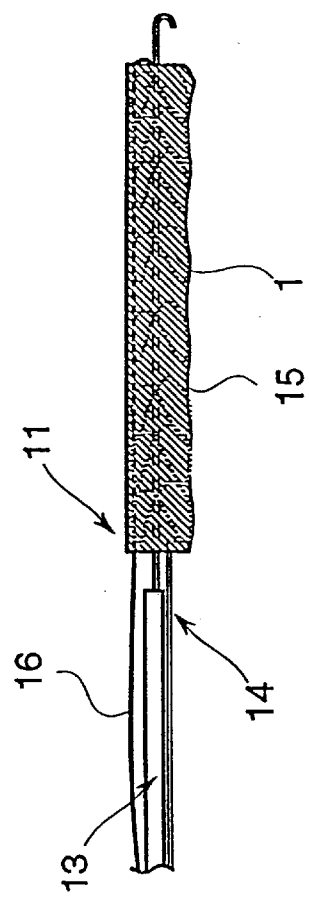
FIG. 22 is a view for explaining the procedure to collapse the artificial blood vessel with the collapsing device.

Then the wrapping member 15 and the artificial blood vessel 1 are restricted from moving by picking the wrapping member 15 and a part of the artificial blood vessel 1 together with a finger at a position shown by an arrow p in FIG. 21. With this condition kept, the cartridge 331 is moved rearward relatively to the position so as to draw the wrapping member 15 and the artificial blood vessel 1 out of the cartridge 331. This makes the artificial blood vessel 1 inserted into inside of the wrapping member 15. Finally, the artificial blood vessel 1 is contained in the wrapping member 15 in a collapsed condition by drawing out the cartridge 331 completely as shown in FIG. 22.

Figure 23:
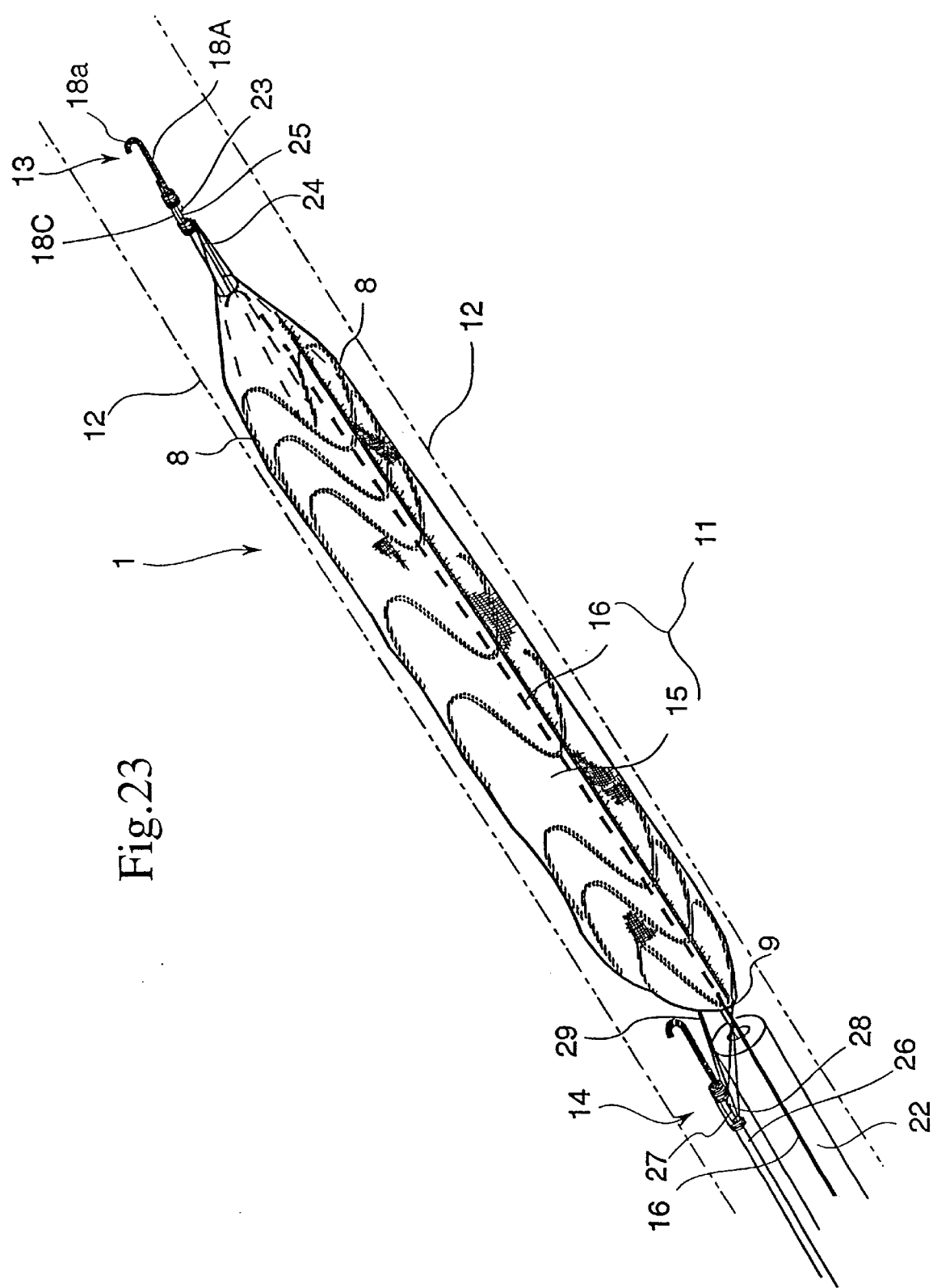
FIG. 23 is a perspective view showing the collapsed artificial blood vessel being held by a retaining means in the embodiment.

FIG. 23 shows the artificial blood vessel 1 which has been collapsed by the use of the retaining means 11 in the above manner.

Next, a procedure to implant the artificial blood vessel 1 having the above arrangement into a target position, namely an affected portion 34 in a human body will be explained.

First, as shown in FIG. 24, for example, introduce the catheter 12 having the seal mechanism 12a at the base end thereof into the body through an inguinal artery at a groin of a thigh as far as the front portion of the catheter 12 locates near the affected portion 34 where an aortic aneurysm or the like is caused. Then introduce the artificial blood vessel 1 collapsed by means of the retaining means 11 into the catheter 12 together with the transporting device 13 and the hauling device 14. Next, push the transporting device 13 forward so as to transport the artificial blood vessel 1 with the hauling device 14 attached thereto by manipulating the base end of the balloon catheter 22 which extends out of the body so as to transport the artificial blood vessel 1 to the target affected portion 34. One end 16a of the wire rod 16 of the retaining means 11, the lock mechanism 20 provided at the base end 13a of the transporting device 13 and the base end 14a of the hauling device extend out of the body through the seal mechanism 12a during the above process.

More concretely, like the first embodiment, transport the artificial blood vessel 1 to near the affected portion 34 by means of the transporting device 13 in a condition that the lock mechanism 20 is locked. And then release the artificial blood vessel 1 from the catheter 12. Since the artificial blood vessel 1 is kept in a collapsed condition by the retaining means 11 after released, it does not necessarily have to be released at a predetermined position and can be adjusted to position at the predetermined position by the use of the transporting device 13 and the hauling device 14, if necessary.

Figure 25:
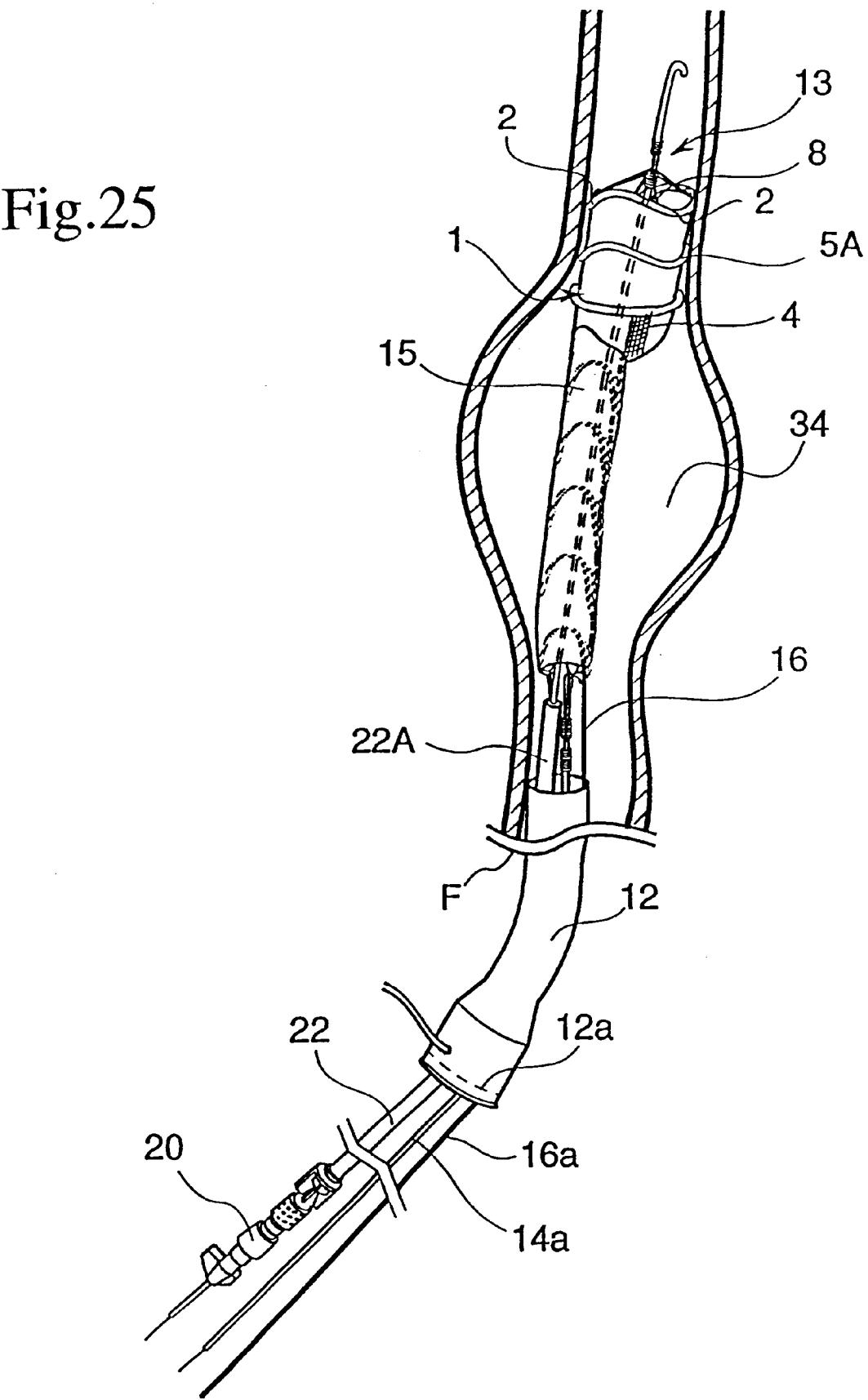
FIG. 25 is an explanatory view showing a step to implant the artificial blood vessel of the embodiment into a target position.

After the artificial blood vessel 1 is arranged at the appropriate position, draw the wire rod 16 which holds the wrapping member 15 of the retaining means 11 as shown in FIG. 25.

Figure 26:
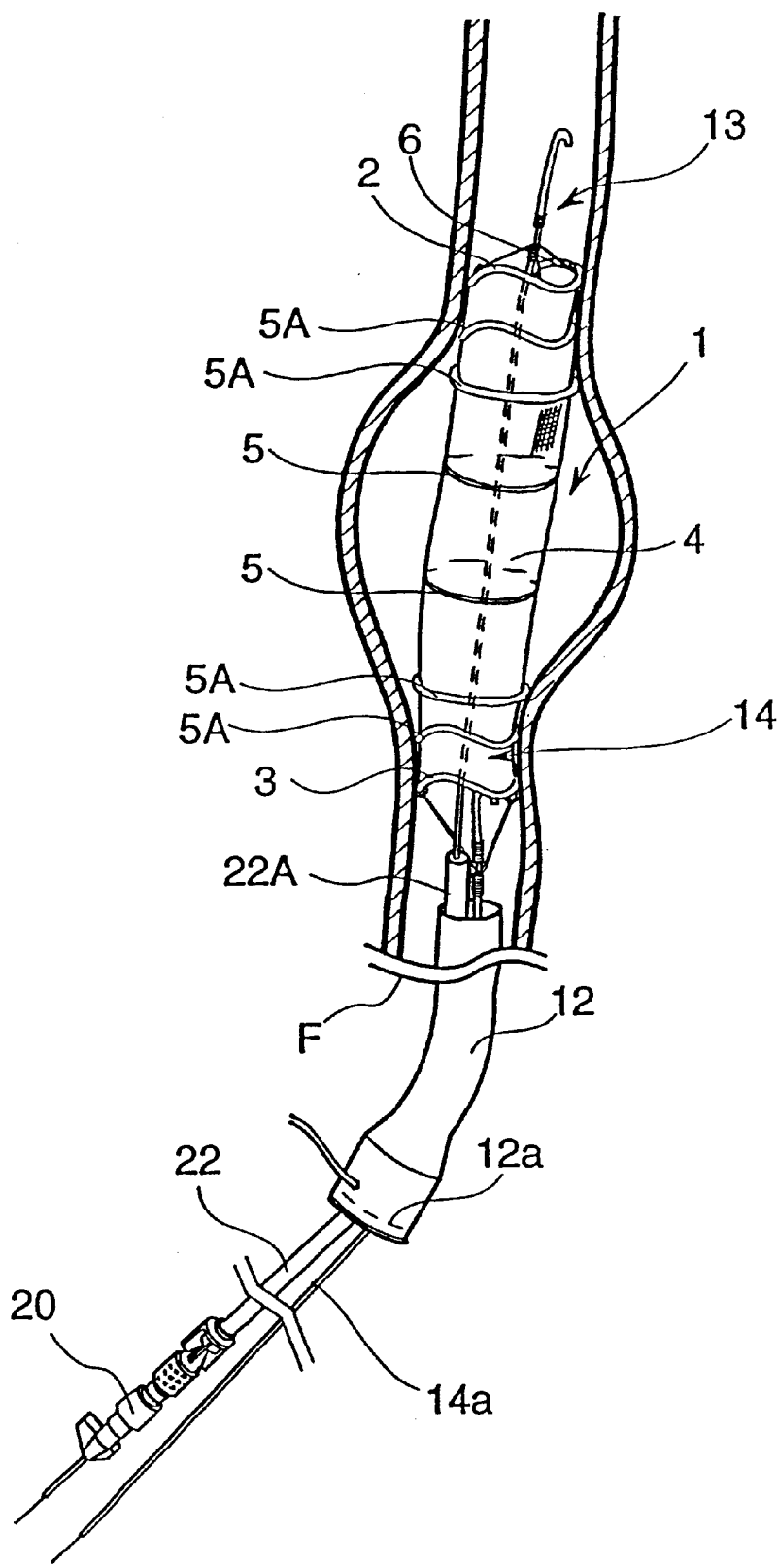
FIG. 26 is an explanatory view showing a step to implant the artificial blood vessel of the embodiment into a target position.

More concretely, first draw the end 16a of the wire rod 16 so as to release the artificial blood vessel 1 from restraint by the wrapping member 15 and inflate each portion of the artificial blood vessel 1 so that the artificial blood vessel 1 tightly attaches to the inner wall of the blood vessel at the affected portion 34 by making use of elasticity. FIG. 26 shows a condition in which the artificial blood vessel 1 is tightly attached to the blood vessel. Finally, like the first embodiment, pull the wire 25 of the transporting device 13 and the wire 27 of the hauling device 14 so as to release engagement of the transporting device 13 and the hauling device 14 with the artificial blood vessel and then draw the transporting device 13 and the hauling device 14 out of the human body. This will complete implantation of the artificial blood vessel 1 into the affected portion 34 as the target position. The wrapping member 15 which has been separated may be left at the position and only the wire rod 16 may be removed, however, the wrapping member 15 may be removed out of the body by capturing it, if necessary.

As mentioned above, with the above procedure, the artificial blood vessel 1 functions effectively as a means to prevent occlusion of the blood vessel at the affected portion 34 by restoring into the predetermined shape after implanted and produces the same effect as that of the first embodiment. Further since the artificial blood vessel 1 is kept in a collapsed condition by the wrapping member 15, the artificial blood vessel 1 can surely be free from deformation during being transported. In addition, since whole of the artificial blood vessel 1 is contained in the wrapping member 15, it is possible to reduce protuberance which is generated locally on an outer face of the collapsed artificial blood vessel 1. This reduces resistance during transportation as much as possible. In addition, if the wrapping member 15 is spread at the affected portion 34, space is formed around the collapsed artificial blood vessel 1, which makes it possible for the artificial blood vessel 1 to be restored into the predetermined shape promptly.

Further, if the artificial blood vessel 1 is collapsed in advance by the use of the retaining means 11, there will be no need of collapsing the artificial blood vessel 1 every time it is used, which makes it possible to introduce the artificial blood vessel 1 into the catheter 12 speedy.

In addition, since the wrapping member 15 is kept in a shape of a tube with sewed by the wire rod 16 and the wrapping member 15 is spread by drawing the wire rod 16, it is possible to keep the wrapping member 15 in a shape of a tube with ease as well as to release a condition of the wrapping member 15 being held directly with relatively little resistance by pulling the wire rod 16 lengthwise. Further, it can be operated to release the wrapping member 15 from a remote place without fail.

The present claimed invention is not limited to the above-described embodiment.

Figure 27:
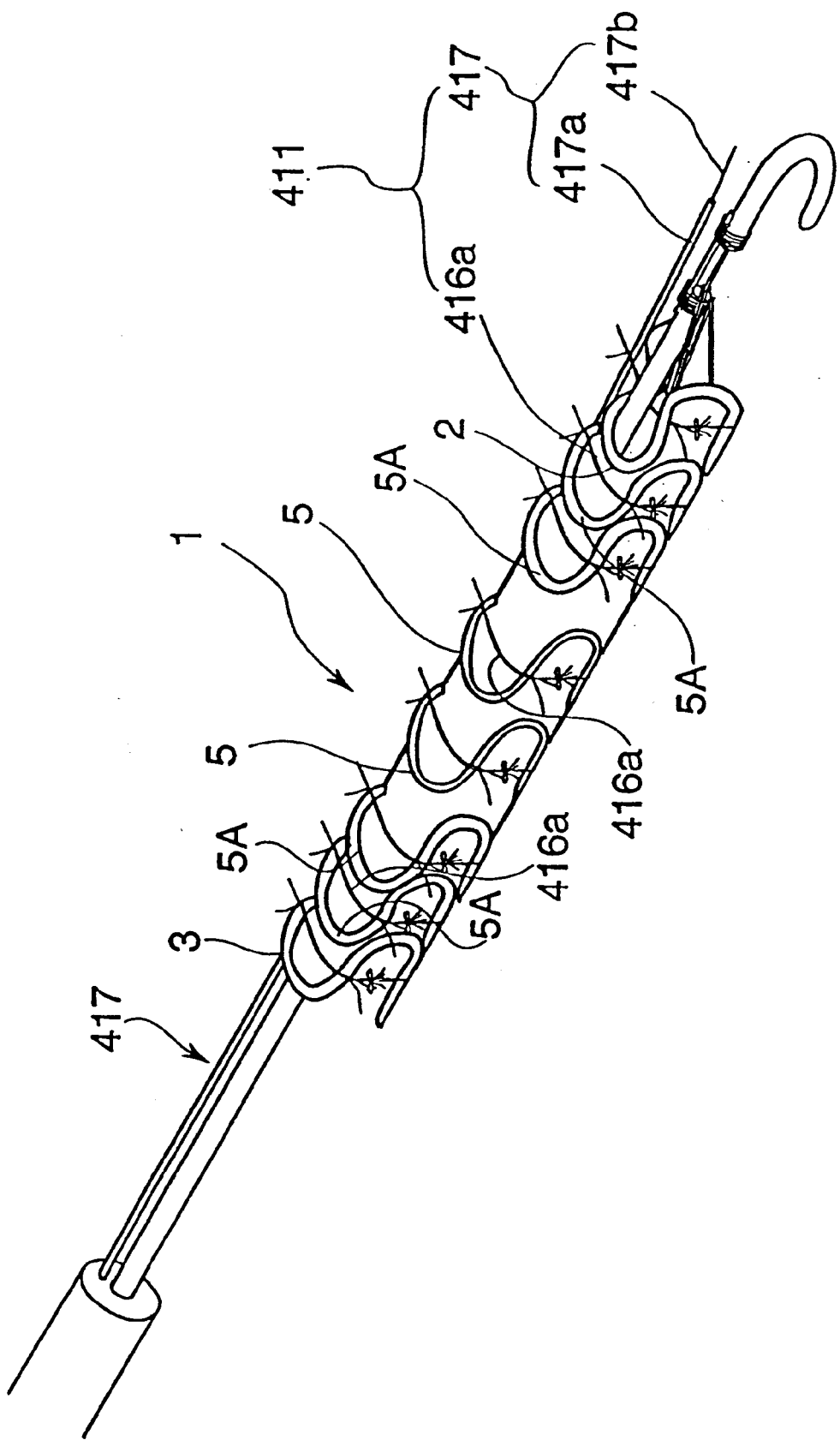
FIG. 27 is a perspective view showing the artificial blood vessel which has previously been folded by means of a string as a modification of the retaining means of the invention.
Figure 28:
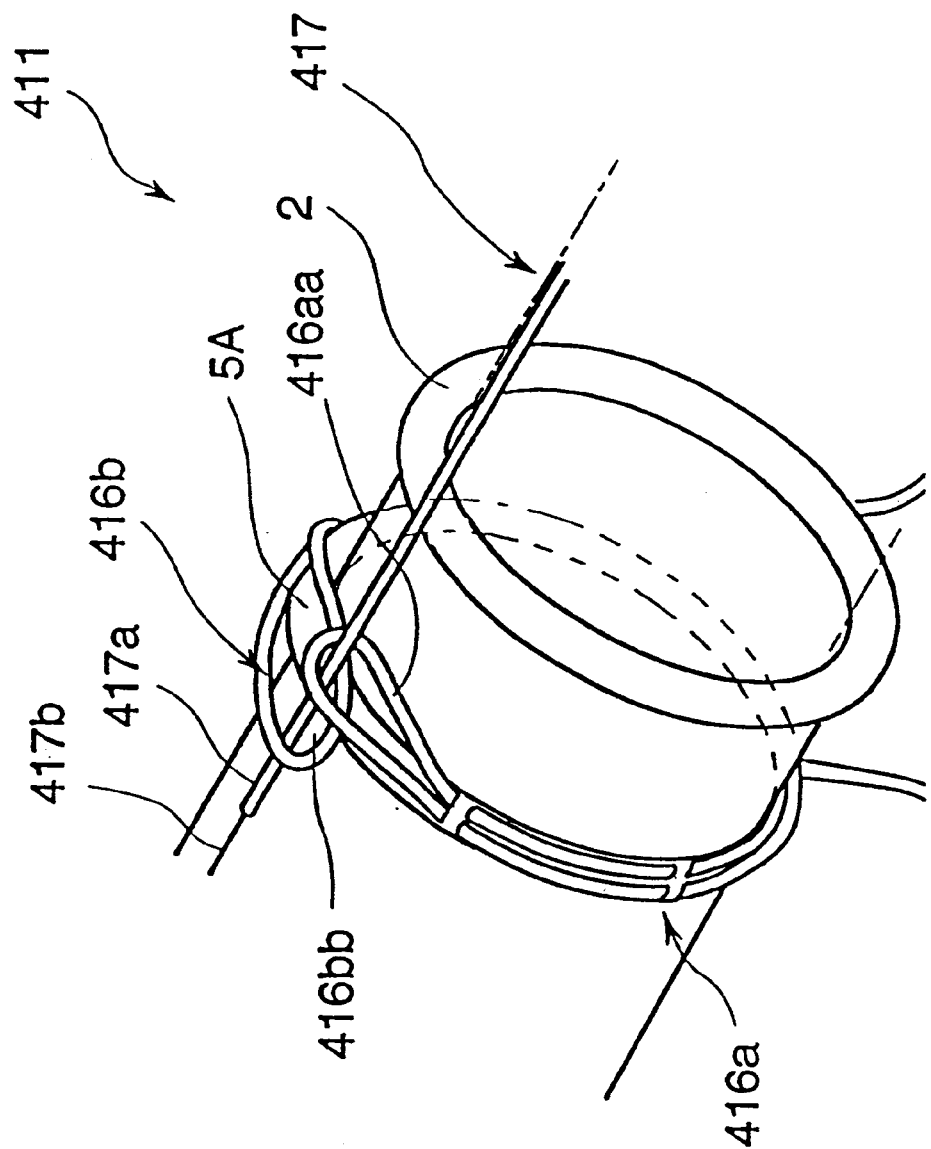
FIG. 28 is a perspective view showing a procedure of collapsing the artificial blood vessel by means of the string.

For example, a retaining means 411 which keeps the artificial blood vessel 1 in a collapsed condition may be as shown in FIGS. 27 and 28. More specifically, a pair of strings 416a for folding the artificial blood vessel 1 are arranged for each of the wire rings 2, 3, 5A, 5 respectively. The intermediate end wire ring 5A is represented for concrete explanation. First, the string 416a is kept folded at the center thereof hooked by a needle for operation or the like. In this state the string 416 is wound around the intermediate end wire ring 5A clockwise by making use of the needle until it reaches the backward of the intermediate end wire ring 5A as shown in FIG. 28, and then sewed up at a plurality of separate positions with the needle. Likewise another string 416b is would around the intermediate end wire ring 5A counterclockwise and then sewed up at positions symmetric to the positions where the string 416a is sewed up. Next, loop portions 416aa, 416bb each formed at each of the tip of a pair of the strings 416a, 416b are overlapped, into which a retaining rod 417 is inserted and then end portions of the strings 416a, 416b are tied together at the backward of the intermediate end wire ring 5A. The artificial blood vessel 1 is helped to be collapsed by a finger or the like, if necessary, so that the intermediate end wire ring 5A is transformed into a wavy shape with the position corresponding to the dividing points 6a, 6c of the intermediate end wire ring 5A forming peaks of forwardly directed peaks. This operation is done to each of the wire rings 2, 3, 5. The consequence is shown in FIG. 27. The retaining rod 417 in this modified example comprises a tube 417a and a wire 417b which is inserted into the tube 417a. The tube 417a is drawn out and only the wire 417b is left after the artificial blood vessel 1 is kept in a collapsed condition. Thus collapsed artificial blood vessel 1 is transported to and implanted into adjacent the target position 34 through the catheter 12 like the first embodiment and restored into the original shape because the artificial blood vessel 1 is released from the collapsed condition by drawing the wire 417b of the retaining rod 417.

With the retaining means 411 having the above arrangement, the same effect is produced as that of the second embodiment. The strings may be a single continuous string. In this case, a wire is arranged along the artificial blood vessel and a string whose one end is fixed to an appropriate position of the artificial blood vessel is wound around the wire clockwise and counterclockwise alternatively and a loop which is formed at another end of the string is passed through the wire. With this arrangement the artificial blood vessel can be released from restraint by the string from a remote place if the wire is drawn out.

Instead of the retaining means 11, 411, the artificial blood vessel may be so arranged to be contained in a pipe in a collapsed condition in advance and to be released from the collapsed condition when it is introduced into the catheter. This arrangement will improve convenience of handling the artificial blood vessel.

The artificial blood vessel may have an arrangement in which parallel arranged two rear end wire rings are arranged to face to a single front end wire ring and a bifurcated tubular cover connects the front end wire ring and two rear end wire rings with forming a Y-shape.

POSSIBLE APPLICATIONS IN INDUSTRY

As mentioned above, the method of collapsing an appliance to be implanted in accordance with the invention can be applied to an appliance to be implanted having value as an artificial blood vessel.

What is claimed is:

1. A method of collapsing an appliance to be implanted, comprising a front end wire ring, a rear end wire ring arranged facing to the front end wire ring, a tubular cover which connects the front end wire ring and the rear end wire ring, and an intermediate wire ring arranged between the front end wire ring and the rear end wire ring, in which each of the wire rings is given flexibly foldable elasticity, and characterized in that circumference of a front end portion of the appliance to be implanted is equally divided into four or an even number over four segments with dividing points between the segments, a front hooking portion for hauling the appliance to be implanted is formed at midpoints between each adjacent two of the dividing points, the front end portion is collapsed into a wavy shape with every other dividing point forming a forwardly directed peak and other dividing point forming a bottom of a forwardly directed valley and the intermediate wire ring and the rear end wire ring are collapsed into a wavy shape having generally the same phase as that of the front end portion.

2. The method of collapsing an appliance to be implanted, described in claim 1 and characterized by that the appliance to be implanted is collapsed in a condition that the intermediate wire ring is fixed to the tubular cover at positions which generally correspond to the positions where the front hooking portions are provided.

3. The method of collapsing an appliance to be implanted, described in claim 1 and characterized by that the collapsed appliance to be implanted is kept in a collapsed condition by a retaining means and the collapsed appliance to be implanted is restored into an original shape by releasing the retaining means at a target position.

4. The method of collapsing an appliance to be implanted, described in claim 3 and characterized by that the retaining means comprises a string which is wound around the collapsed appliance to be implanted and which has a loop at one portion thereof and a retaining rod which passes through the loop of the string, the appliance to be implanted is kept in the collapsed condition by passing the retaining rod through the loop of the string and the collapsed condition kept by means of the string can be released by drawing the retaining rod out of the loop.

5. The method of collapsing an appliance to be implanted, described in claim 1 and characterized by that the appliance to be implanted has a rear hooking portion for hauling the appliance to be implanted at a position which has generally the same phase as that of the front hooking portion on a rear end portion of the appliance to be implanted and the appliance to be implanted is collapsed so that the rear hooking portion locates at midpoints between the forwardly directed peaks and the bottoms of forwardly directed valleys when the rear end portion is collapsed to have generally the same phase as that of the front end portion.

6. The method of collapsing an appliance to be implanted, described in claim 1 and characterized by that the appliance to be implanted has a rear hooking portion for hauling the appliance to be implanted at every other position which has generally the same phase as that of the dividing points on a rear end portion of the appliance to be implanted and the appliance to be implanted is collapsed so that the rear hooking portion locates at the bottoms of the forwardly directed valleys of the rear end portion when the rear end portion is collapsed to have generally the same phase as that of the front end portion.

7. The method of collapsing an appliance to be implanted, described in claim 1 and characterized by that the front and rear end wire rings are connected with the tubular cover through a film member so that an annular gap at least formed between each of the front and rear end wire rings and the tubular cover is liquid-tightly sealed and the appliance to be implanted is collapsed with each of the front and rear wire rings making a back and forth movement relative to the tubular cover within a certain range.

8. The method of collapsing an appliance to be implanted, described in claim 1 and characterized by that a number of the dividing point is four.

9. The method of collapsing an appliance to be implanted, described in claim 1 and characterized by that the appliance to be implanted is an artificial blood vessel.

10. An appliance to be implanted comprising a front end wire ring arranged at a front end portion of the appliance to be implanted, a rear end wire ring arranged at a rear end portion thereof so as to face to the front end wire ring, a tubular cover which connects the front end wire ring and the rear end wire ring and an intermediate wire ring arranged between the front end wire ring and the rear end wire ring, in which each of the wire rings is given flexibly foldable elasticity and folded into a wavy shape having forwardly directed peaks and bottoms of forwardly directed valleys continuously and alternatively and the appliance to be implanted is transported by being hauled forward with this condition kept, and characterized by that a front hooking portion for hauling the appliance to be implanted is provided at a general-midpoint between the peak and the bottom of the adjacent valley on the front end portion of the appliance to be implanted.

11. The appliance to be implanted, described in claim 10 and characterized by that the intermediate wire ring is fixed to the tubular cover at positions which generally correspond to the positions where the front hooking portions are provided.

12. The appliance to be implanted, described in claim 10 and characterized by that rear hooking portions for hauling the appliance to be implanted are provided at the rear end portion of the appliance to be implanted at positions which have the same phase as that of the front hooking portion provided at the front end portion of the appliance to be implanted and a number of the rear hooking portion is the same as that of the front hooking portion.

13. The appliance to be implanted, described in claim 10 and characterized by that rear hooking portions for hauling the appliance to be implanted are provided at the rear end portion of the appliance to be implanted at every other positions which have the same phase as that of the front hooking portion provided at the front end portion of the appliance to be implanted and a number of the rear hooking portion is half the number of the front hooking portion.

14. The appliance to be implanted, described in claim 10 and characterized by that at least each of the front end wire ring and the rear end wire ring is connected with the tubular cover through a film member so that each of the front end wire ring and the rear end wire ring can make a back and forth movement relative to the tubular cover within a certain range and an annular gap formed between the front end wire ring and the tubular cover or between the rear end wire ring and the tubular cover is liquid-tightly sealed.

15. The appliance to be implanted, described in claim 10 and characterized by that a number of the dividing point is four.

16. The appliance to be implanted, described in claim 10 and characterized by that the appliance to be implanted is an artificial blood vessel.

17. An appliance to be implanted comprising a front end wire ring arranged at a front end portion of the appliance to be implanted, a rear end wire ring arranged at a rear end portion thereof so as to face to the front end wire ring, a tubular cover which connects the front end wire ring and the rear end wire ring and an intermediate wire ring arranged between the front end wire ring and the rear end wire ring, in which each of the wire rings is given flexibly foldable elasticity and folded into a wavy shape having forwardly directed peaks and bottoms of forwardly directed valleys continuously and alternatively and the appliance to be implanted is transported by being hauled forward with this condition kept, and characterized by that front hooking portions for hauling the appliance to be implanted are provided at positions located at general-midpoints between adjacent dividing points, wherein the dividing points divide the circumference of the front end portion into four segments and wherein each dividing point forms a peak or a valley, and rear hooking portions for hauling the appliance to be implanted are provided at four positions on the rear end portion of the appliance to be implanted wherein each of the four positions has the same phase as that of the front hooking portion.

18. An appliance to be implanted comprising a front end wire ring arranged at a front end portion of the appliance to be implanted, a rear end wire ring arranged at a rear end portion thereof so as to face to the front end wire ring, a tubular cover which connects the front end wire ring and the rear end wire ring and an intermediate wire ring arranged between the front end wire ring and the rear end wire ring, in which each of the wire rings is given flexibly foldable elasticity and folded into a wavy shape having forwardly directed peaks and bottoms of forwardly directed valleys continuously and alternatively and the appliance to be implanted is transported by being hauled forward with this condition kept, and characterized by that front hooking portions for hauling the appliance to be implanted are provided at positions located at general-midpoints between adjacent dividing points, wherein the dividing points divide the circumference of the front end portion into four segments and wherein each dividing point forms a peak or a valley, rear hooking portions for hauling the appliance to be implanted are provided at two positions on circumference of the rear end portion of the appliance to be implanted or near the two positions wherein each of the two positions locates at the bottoms of forwardly directed valleys.

19. An appliance to be implanted comprising a front end wire ring arranged at a front end portion of the appliance to be implanted, a rear end wire ring arranged at a rear end portion thereof so as to face to the front end wire ring, a tubular cover which connects the front end wire ring and the rear end wire ring and an intermediate wire ring arranged between the front end wire ring and the rear end wire ring, in which each of the wire rings is given flexibly foldable elasticity and folded into a wavy shape having forwardly directed peaks and bottoms of forwardly directed valleys continuously and alternatively and the appliance to be implanted is transported by being hauled forward with this condition kept, and characterized by that front hooking portions for hauling the appliance to be implanted are provided at positions located at general-midpoints between adjacent dividing points, wherein the dividing points divide the circumference of the front end portion into four segments and wherein each dividing point forms a peak or a valley, a transporting device wherein a wire passes into a tube and a front portion of the wire is selectively exposable through an opening portion provided on the tube so as to engage and disengage the front hooking portions.

20. An appliance to be implanted comprising a front end wire ring arranged at a front end portion of the appliance to be implanted, a rear end wire ring arranged at a rear end portion thereof so as to face to the front end wire ring, a tubular cover which connects the front end wire ring and the rear end wire ring and an intermediate wire ring arranged between the front end wire ring and the rear end wire ring, in which each of the wire rings is given flexibly foldable elasticity and folded into a wavy shape having forwardly directed peaks and bottoms of forwardly directed valleys continuously and alternatively and the appliance to be implanted is transported by being hauled forward with this condition kept, and characterized by that front hooking portions for hauling the appliance to be implanted are provided at positions each of which locates at a general-midpoint between a dividing point and an adjacent dividing point wherein the dividing points divide the circumference of the front end portion into an even number over four segments and the front portion is collapsed into a wavy shape with every other dividing point forming a forwardly directed peak and the adjacent dividing point forming a bottom of a forwardly directed valley and other intermediate wire ring and the rear end wire ring are collapsed into a wavy shape having the same phase as that of the front end portion and the appliance to be implanted is kept in a collapsed condition by a releasable retaining means with the above condition kept.

21. The appliance to be implanted, described in claim 20 and characterized by that the retaining means is so arranged to release the appliance to be implanted from a collapsed condition by drawing a part of the retaining means out of the retaining means.

22. The appliance to be implanted, described in claim 21 and characterized by that the retaining means comprises a string having a loop at one portion thereof and a retaining rod which is to pass through the loop of the string and the appliance to be implanted is kept in a collapsed condition with the retaining rod passing through the loop of the string and the appliance to be implanted can be released from the collapsed condition by drawing the retaining rod out of the loop.

* * * * *

UNITED STATES PATENT AND TRADEMARK OFFICE
CERTIFICATE OF CORRECTION

PATENT NO.    : 6,514,282 B1
DATED         : February 4, 2003
INVENTOR(S)   : Kanji Inoue It is certified that error appears in the above-identified patent and that said Letters Patent is hereby corrected as shown below:

<u>Title page,</u>
Item [54], "METHOD OF FOLDING TRANSPLANTING INSTRUMENT AND TRANSPLANTING INSTRUMENT" has been replaced with -- METHOD OF COLLAPSING AN APPLIANCE AND THE APPLIANCE TO BE IMPLANTED --;
Item [56], References Cited, FOREIGN PATENT DOCUMENTS,
"JP 0 464 755 A1 1/1992" has been replaced with -- EP 0 464 755 A1 --;

<u>Column 19,</u>
Line 49, -- end -- has been inserted after "rear".

Signed and Sealed this

Twenty-first Day of October, 2003

JAMES E. ROGAN
*Director of the United States Patent and Trademark Office*